US008460692B2

(12) United States Patent
Zhang et al.

(10) Patent No.: US 8,460,692 B2
(45) Date of Patent: Jun. 11, 2013

(54) ALGINATE-BASED NANOFIBERS AND RELATED SCAFFOLDS

(75) Inventors: Miqin Zhang, Bothell, WA (US); Narayan Bhattarai, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/370,016

(22) Filed: Feb. 9, 2012

(65) Prior Publication Data

US 2012/0141558 A1 Jun. 7, 2012

Related U.S. Application Data

(60) Division of application No. 12/239,478, filed on Sep. 26, 2008, now Pat. No. 8,147,858, which is a continuation of application No. PCT/US2007/065388, filed on Mar. 28, 2007.

(60) Provisional application No. 60/787,099, filed on Mar. 28, 2006.

(51) Int. Cl.
*A61F 13/00* (2006.01)
*A61K 9/00* (2006.01)

(52) U.S. Cl.
CPC .................................. *A61K 9/0024* (2013.01)
USPC ........................................................ 424/422

(58) Field of Classification Search
CPC .................................................... A61K 9/0024
USPC ........................................................ 424/422
See application file for complete search history.

(56) References Cited

U.S. PATENT DOCUMENTS

| 6,753,454 | B1 | 6/2004 | Smith et al. |
| 2003/0017208 | A1 | 1/2003 | Ignatious |
| 2004/0018226 | A1 | 1/2004 | Wnek |
| 2004/0058887 | A1 | 3/2004 | Bowlin |
| 2005/0136253 | A1 | 6/2005 | Michael |
| 2006/0083784 | A1 | 4/2006 | Ignatious |

FOREIGN PATENT DOCUMENTS

| JP | 4-82918 A | 3/1992 |
| WO | 2004/035885 A1 | 4/2004 |
| WO | WO 2005000169 A2 * | 1/2005 |

OTHER PUBLICATIONS

Derwent English Abstract of JP 04-082918A (pp. 1-3) 1992.*
English Abstract of JP-04-082918 (1992) from www.sumobrain.com (pp. 1-2).*
Bhattarai, N., et al., "Alginate-Based Nanofibrous Scaffolds: Structural, Mechanical, and Biological Properties," Advanced Materials 18(11):1463-1467, Apr. 2006.
Bhattarai, N., et al., "Electrospun Chitosan-Based Nanofibers and Their Cellular Compatibility," Biomaterials 26(31):6176-6184, Nov. 2005.
Caykara, T., et al., "Poly(ethylene oxide) and Its Blends With Sodium Alginate," Polymer 46(24):10750-10757, Nov. 2005.

(Continued)

*Primary Examiner* — Bethany Barham
(74) *Attorney, Agent, or Firm* — Christensen O'Connor Johnson Kindness PLLC

(57) ABSTRACT

Alginate nanofibers, scaffolds that include alginate nanofibers, implantable devices that include alginate nanofibers, and methods for making the alginate nanofibers by electrospinning.

19 Claims, 18 Drawing Sheets

OTHER PUBLICATIONS

Jin, H.-J., et al., "Electrospinning Bombyx rnori Silk with Poly(ethylene oxide)," Biomacromolecules 3(6):1233-1239, 2002.

Lu, J.-W., et al., "Electrospinning of Sodium Alginate With Poly(ethylene oxide)," Polymer 47(23):8026-8031, Oct. 2006.

Safi, S., et al., "Study of Electrospinning of Sodium Alginate, Blended Solutions of Sodium Alginate/Poly(vinyl alcohol) and Sodium Alginate/Poly(ethylene oxide)," Journal of Applied Polymer Science 104(5):3245-3255, 2007.

* cited by examiner

ALGINATE-BASED NANOFIBERS AND RELATED SCAFFOLDS

CROSS-REFERENCE TO RELATED APPLICATION

This application is a division of U.S. patent application Ser. No. 12/239,478, filed Sep. 26, 2008, which is a continuation of International Application No. PCT/US2007/065388, filed Mar. 28, 2007, which claims the benefit of U.S. Provisional Application No. 60/787,099, filed Mar. 28, 2006. Each application is expressly incorporated herein by reference in its entirety.

STATEMENT OF GOVERNMENT LICENSE RIGHTS

The invention was made with government support under Contract No. EEC 9529161, awarded by the National Science Foundation. The government has certain rights in the invention.

BACKGROUND OF THE INVENTION

Polymeric nanofibers can be used for a broad spectrum of biological and medical applications. They are of particular interest in regenerative medicine and tissue engineering because they can be potentially tailored to mimic the natural extracellular matrix (ECM) in terms of structure, chemical composition, and mechanical properties. In this context, they serve as scaffolds to direct cellular behavior and function until host cells can repopulate and resynthesize a new natural matrix. The ECM molecular network surrounding the cells provides mechanical support and regulates cellular activities. The natural ECM in human tissue is mainly composed of proteoglycans (glycosaminoglycan (GAG)) and fibrous proteins, both with nanoscale structural dimensions. Studies have shown that scaffolds with nanoscale structures support cell adhesion and proliferation, and function better than their microscale counterparts.

A number of synthetic polymer nanofibers with fiber diameters from a few tens to a few hundreds of nanometers have been fabricated for tissue engineering; these include polyglycolide (PGA), poly(L-lactic acid) (PLA), and their copolymers poly(glycolide-co-lactide) (PLGA) and poly($\epsilon$-caprolactone) (PCL). The studies demonstrated favorable biological responses of seeded cells, such as enhanced cell attachment and in vitro proliferation. Recently, there has been growing interest in the synthesis of natural polymer-based nanofibers because of their proven biocompatibility and their resorbable biodegradation products. Advantageous attributes of natural polymers include hydrophilicity, non-toxicity, less-immune reaction, as well as enhanced cell adhesion and proliferation. Collagen, gelatin, hyaluronan, chitosan, and alginate are the most commonly used natural polymers in tissue engineering. In a few recent studies, collagen and chitosan have been successfully fabricated into nanofibers and have demonstrated good cellular compatibility. The ability to generate nanofibrous matrices from natural polymers, especially those derived from plants, may provide virtually unlimited resources for the development of tissue-compatible scaffolds for functional restoration of damaged or dysfunctional tissues. This restoration currently relies mainly on the autograft and allograft procedures—surgical procedures facing the challenges of limited resources, risk of infection, and viral transmission.

SUMMARY OF THE INVENTION

The present invention provides alginate-based nanofibers, scaffolds that include nanofibers, implantable devices that include the nanofibers, and methods for making the nanofibers by electrospinning.

In one aspect, the invention provides an alginate-based fiber. In one embodiment, the fiber includes alginate and has a diameter of from about 20 to about 2000 nm. In one embodiment, the fiber has a diameter from about 50 to about 500 nm. In addition to alginate, the alginate-based fiber of the invention includes a hydrophilic polymer to facilitate production of the fiber by electrospinning.

In one embodiment, the fiber includes from about 30 to about 95 weight percent alginate based on the total weight of the fiber. In one embodiment, about 80 weight percent alginate based on the total weight of the fiber.

Hydrophilic polymers useful in making the fiber of the invention include poly(alkylene oxide) polymers, polyvinyl alcohol polymers, and polycarboxylic acid polymers. Representative poly(alkylene oxide) polymers include polyethylene oxide polymers and block copolymers (for example, nonionic block copolymers commercially available under the designation PLURONIC and/or POLOXAMER). In one embodiment, the hydrophilic polymer (e.g., poly(alkylene oxide)) has a molecular weight of from about 50 kDa to about 1000 kDa. In one embodiment, the fiber includes from about 5 to about 30 weight percent poly(alkylene oxide) based on the total weight of the fiber. In one embodiment, the fiber includes about 20 weight percent poly(alkylene oxide) based on the total weight of the fiber.

The fiber of the invention can be crosslinked to maintains its structural integrity in aqueous and biological environments.

In one embodiment, the fiber of the invention is crosslinked with an ionic crosslinking agent. Suitable ionic crosslinking agents include a metal ions reactive toward alginate carboxylic acid groups. Representative metal ions include calcium (2), barium (2), strontium (2), copper (2), zinc (2), magnesium (2), manganese (2), cobalt (2), lead (2), iron (3), and aluminum (3) ions.

In one embodiment, the fiber of the invention is crosslinked with a covalent crosslinking agent. Suitable covalent crosslinking agents include bifunctional crosslinking agents reactive toward alginate hydroxyl and/or carboxylic acid groups. Representative covalent crosslinking agents include carbodiimides, allyl halide oxides, dialdehydes, diamines, and diisocyanates. In certain embodiments, the covalent crosslinking agent is selected from epichlorohydrin, gluteraldehyde, hexamethylene diisocyanate, adipic acid hydrazide, and 1-ethyl-3-(3-dimethylaminopropyl)carbodiimide hydrochloride.

In one embodiment, the fiber of the invention is both ionically crosslinked and covalently crosslinked.

In one embodiment, the fiber of the invention has a Young's modulus of from about 0.004 to about 40 MPa.

In one embodiment, the fiber includes from about 30 to about 95 weight percent alginate and from about 5 to about 70 weight percent polyethylene oxide. In one embodiment, the fiber includes about 80 weight percent alginate and about 20 weight percent polyethylene oxide.

In another aspect of the invention, fibrous scaffolds are provided. The fibrous scaffolds of the invention include a plurality of the fibers of the invention, as described above.

In one embodiment, the scaffold having a thickness of from about 0.05 to about 5 mm.

The scaffolds can include one or more materials other than the fibers of the invention.

In one embodiment, the scaffold further includes chitosan. In this embodiment, the scaffold includes from about 0.5 to about 15 weight percent chitosan.

In one embodiment, the scaffold further includes collagen. In this embodiment, the scaffold includes from about 0.5 to about 20 weight percent chitosan.

In one embodiment, the scaffold further includes a biologically active amino acid molecule. Representative amino acid molecules include growth factors, fibronectin, laminin, vitronectin, integrins, nucleic acid molecules, lipids, sugars, antisense molecules, anti-inflammatory agents, immunomodulatory agents, molecules that promote cell migration, molecules that promote cell division, molecules that promote cell proliferation and differentiation, molecules that stimulate phenotypic modification of cells, molecules that promote angiogenesis, molecules that promote vascularization, and molecules that promote extracellular matrix disposition.

In one embodiment, the scaffold further includes a signaling ligand. Representative signaling ligands include members of the TGF-β family, bone morphogenic proteins, fibroblast growth factors-1 and -2, platelet-derived growth factor-AA and -BB, and platelet rich plasma and vascular endothelial cell-derived growth factor. In this embodiment, the scaffold includes from about 1 to about 100 ng signaling ligand per gram scaffold.

In a further aspect of the invention, implantable devices are provided. The implantable devices include the fibers and/or the scaffolds of the invention described above. Representative implantable devices include cell transplantation devices, drug delivery devices, wound dressings and hemostats, surgically implantable devices for repairing damaged cartilage in mammalian articulating joints, fabric barriers to hyperplasia and tissue adhesion, vascular prostheses, nerve grafts, spinal fusion cages, and skin substitutes.

In another aspect, the invention provides a method for making the alginate fibers of the invention. In one embodiment, the method includes (a) generating an electrostatic field between a first electrode and a second electrode; and (b) electrospinning an aqueous alginate solution comprising alginate and a hydrophilic polymer onto a collection surface located between the first electrode and the second electrode to provide a plurality of alginate fibers on the collection surface.

In one embodiment, the alginate solution includes from about 1 to about 8 percent by weight alginate. In one embodiment, the alginate solution includes from about 3 to about 5 percent by weight alginate.

In one embodiment, the hydrophilic polymer is selected from a poly(alkylene oxide), a polyvinyl alcohol, and a polycarboxylic acid polymer. In one embodiment, the alginate solution includes from about 1 to about 10 percent by weight poly(alkylene oxide). In one embodiment, the alginate solution includes from about 2 to about 4 percent by weight poly(alkylene oxide). In one embodiment, the poly(alkylene oxide) is polyethylene oxide.

In one embodiment, the ratio of alginate to poly(alkylene oxide) is from about 70:30 to about 95:5. In one embodiment, the ratio of alginate to poly(alkylene oxide) is about 80:20.

In one embodiment, the alginate solution further includes a co-solvent. Suitable co-solvents are polar aprotic solvents. Representative co-solvents include 1,4-dioxane, tetrahydrofuran, acetone, acetonitrile, dimethylformamide, and dimethylsulfoxide. In one embodiment, the co-solvent is dimethylsulfoxide. In one embodiment, the co-solvent is present in the solution in an amount from about 0.5 to about 20 weight percent. In one embodiment, the co-solvent is present in the solution in an amount from about 1 to about 10 weight percent. In one embodiment, the co-solvent is present in the solution in about 5 weight percent.

In one embodiment, the alginate solution further includes a surfactant. Suitable surfactants include glycol stearate, cocoamide surfactants, and polyoxyethylene(10) isooctylphenyl ether (Triton X-100 family). In one embodiment, the surfactant is present in the solution in an amount from about 0.01 to about 1.0 weight percent. In one embodiment, the surfactant is present in the solution in about 0.05 weight percent. In one embodiment, the surfactant is polyoxyethylene(10) isooctylphenyl ether.

In one embodiment, the alginate solution includes both a co-solvent and a surfactant, as described above.

In one embodiment, the zero shear viscosity of the alginate solution is from about 2.0 to about 8.0 Pa·s.

In one embodiment, the method further includes treating the plurality of alginate fibers with an ionic crosslinking agent to provide a plurality of ionically crosslinked alginate fibers. Suitable ionic crosslinking agents are described above and include metal ions, such as calcium (2) ion, barium (2) ion, strontium (2), copper (2), zinc (2), magnesium (2), manganese (2), cobalt (2), lead (2), iron (3), and aluminum (3) ions.

In one embodiment, the method further includes treating the plurality of ionically crosslinked alginate fibers with a covalent crosslinking agent to provide a plurality of covalently crosslinked alginate fibers. Suitable covalent crosslinking agents are described above and include carbodiimides, allyl halide oxides, dialdehydes, diamines, and diisocyanates.

The fibers of the invention can be crosslinked ionically, covalently, or ionically and covalently. In one embodiment, the method of the invention includes treating the alginate fibers with a covalent crosslinking agent to provide a plurality of covalently crosslinked alginate fibers.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 1A is an image of a representative alginate-PEO fiber spun from a solution having an alginate/PEO ratio of 70:30; FIG. 1A' is a higher magnification image of the image of FIG. 1A; FIG. 1B is an image of a representative alginate-PEO fiber spun from a solution having an alginate/PEO ratio of 80:20; FIG. 1B' is a higher magnification image of the image of FIG. 1B; FIG. 1C is an image of a representative alginate-PEO fiber spun from a solution having an alginate/PEO ratio of 90:10; and FIG. 1A' is a higher magnification image of the image of FIG. 1A.

fibers of the invention electrospun from an 80:20 alginate/ PEO solution after immersion in deionized (DI) water for 1 day and 15 days, respectively.

Figure 3A:
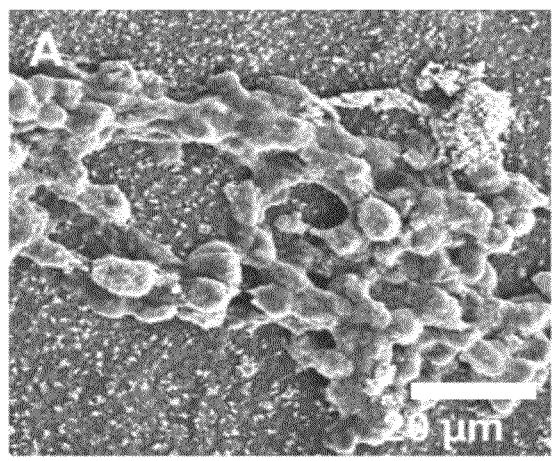
Figure 3B:
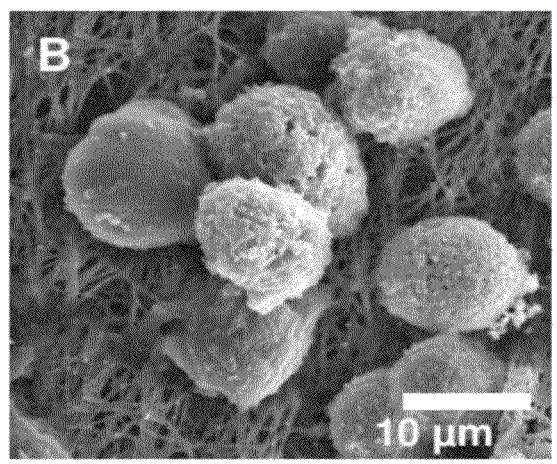
Figure 3C:
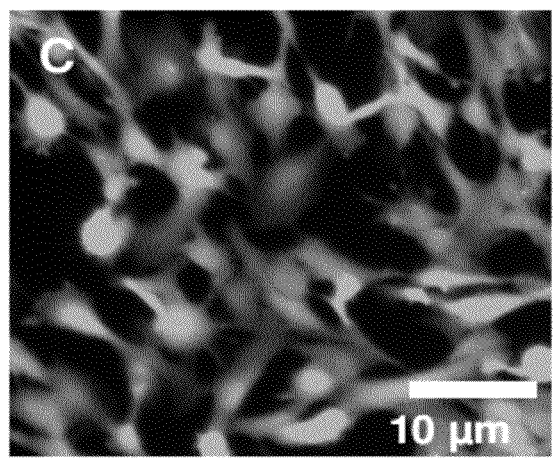

FIGS. 3A-3C compare the in vitro cellular compatibility of alginate fibers electrospun from an 80:20 alginate/PEO solution: FIG. 3A is a scanning electron microscope image of chondrocytes grown on alginate-PEO fibers; FIG. 3B is a higher magnification image of the image of FIG. 3B; and FIG. 3C is a fluorescence image of cells on fibers with the Live/Dead cell stain.

Figure 4:
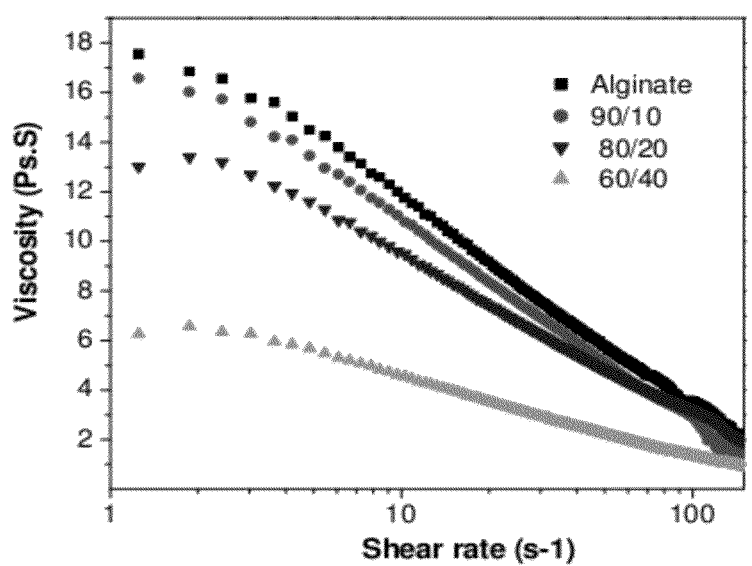

FIG. 4 is a graph comparing shear viscosities of polymer solutions having different alginate/PEO weight ratios (100:0; 90:10; 80:20; and 60:40) as a function of shear rate.

FIGS. 5A-5D are SEM images of electrospun structures from alginate solutions having alginate/PEO ratios of 90:10; 80:20; 70:30; and 60:40, respectively.

Figure 6A:
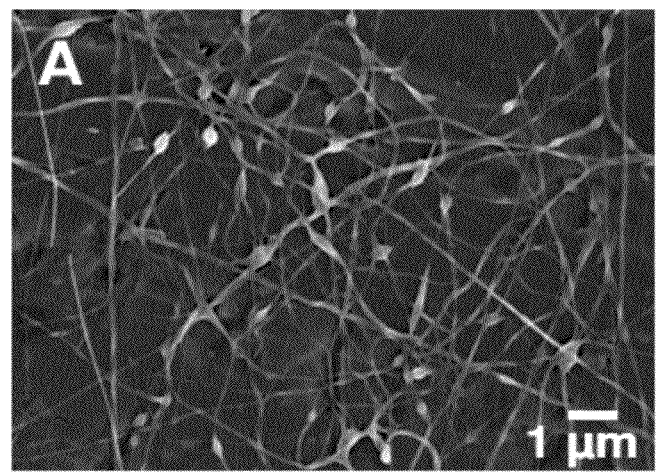
Figure 6B:
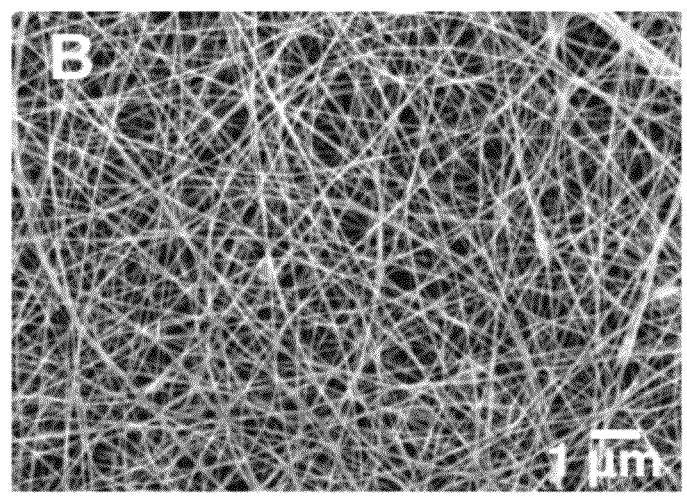
Figure 6C:
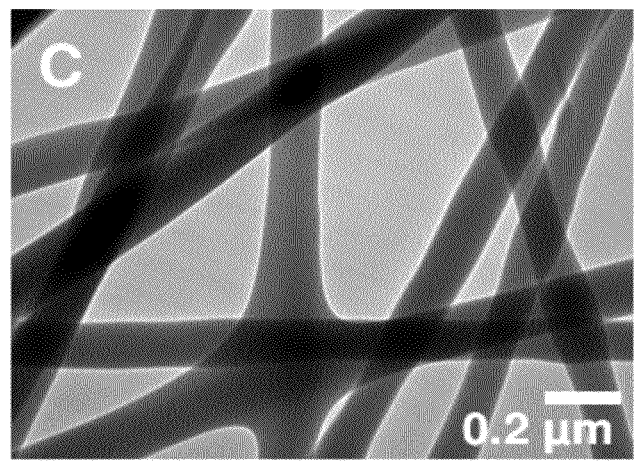
Figure 6D:
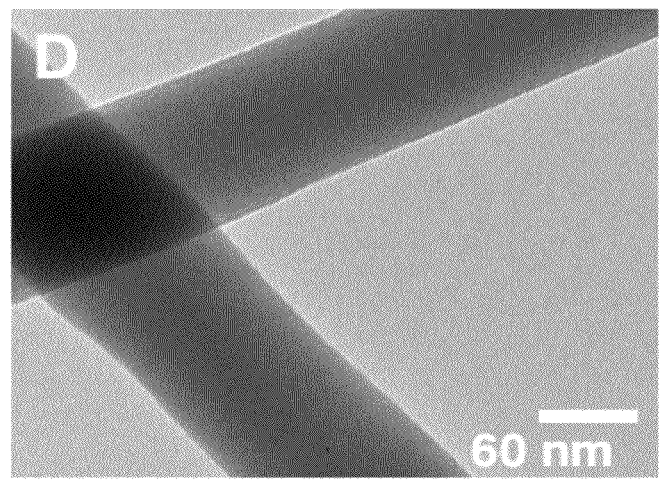

FIGS. 6A-6D are images of electrospun alginate/PEO fibers from 80:20 alginate/PEO solutions: FIG. 6A is a SEM image of fibers obtained by adding Triton X-100 (0.5 wt %); FIG. 6B is a SEM image of fibers obtained by adding Triton X-100 (0.5 wt %) and DMSO (5.0 wt %); FIG. 6C is a transmission electron microscope (TEM) image of the fibers of FIG. 6B; and FIG. 6D is a higher magnification TEM image of the fibers of FIG. 6B.

Figure 7A:
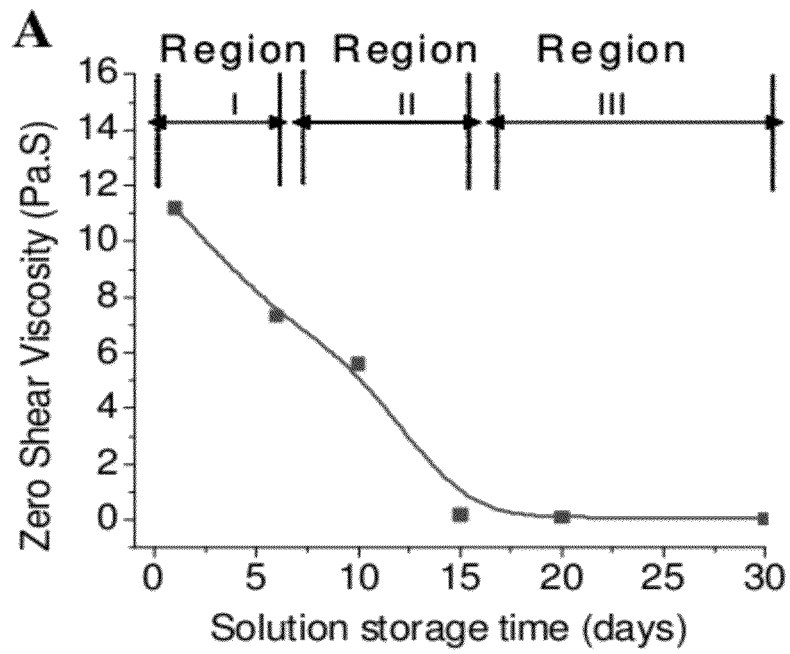

FIG. 7A is a graph illustrating zero shear viscosity of a 4 wt % alginate solution as a function of storage time.

Figure 7B:
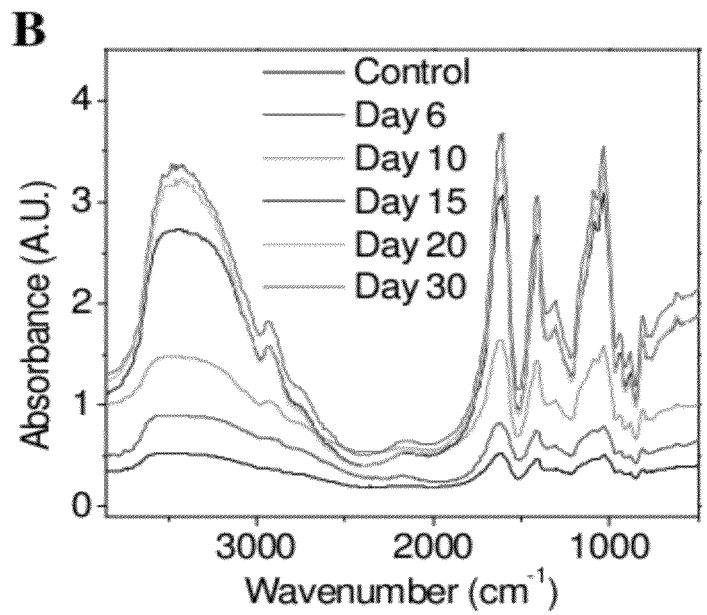

FIG. 7B compares the infrared (FTIR) spectra of the 4 wt % alginate solution as a function of storage time (Day 6, 10, 15, 20, and 30) to the infrared spectrum of as-received alginate powder (Control).

Figure 7C:
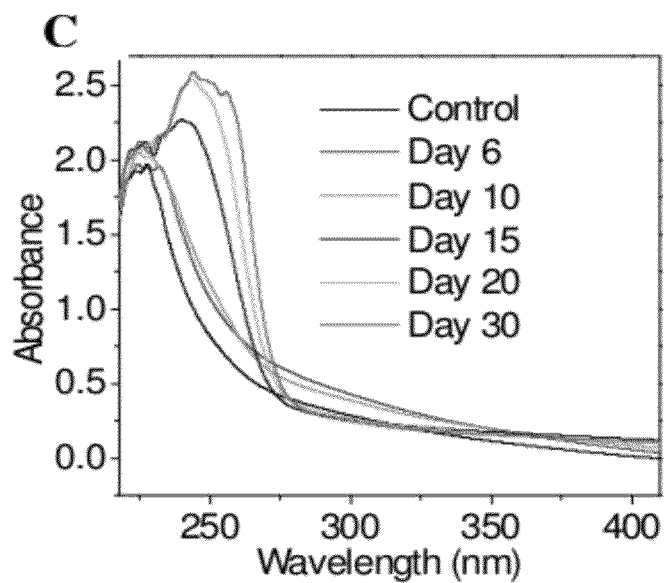

FIG. 7C compares the ultraviolet (UV) absorbance spectra of the 4 wt % alginate solution as a function of storage time (Day 6, 10, 15, 20, and 30) to the absorbance spectrum of as-received alginate powder (Control).

Figure 7D:
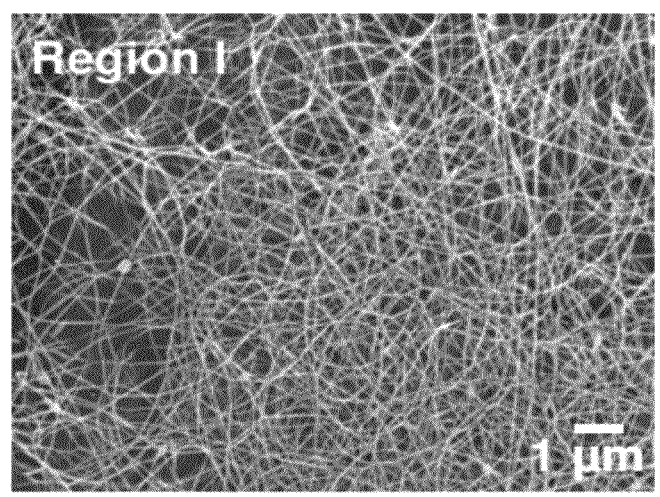
Figure 7E:
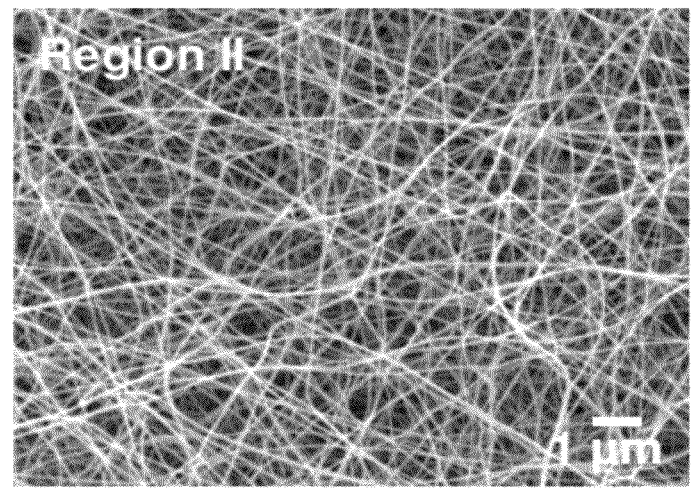
Figure 7F:
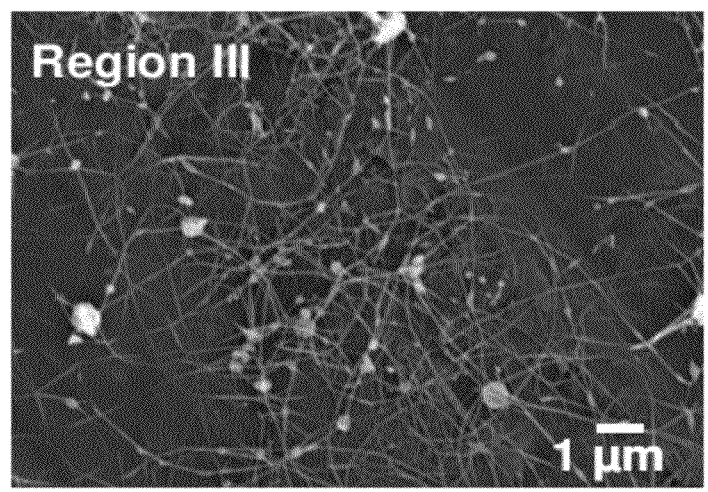

FIGS. 7D-7F are SEM images of fibers electrospun from alginate solutions having viscosities in Regions I, II, and III, respectively, of FIG. 7A.

Figure 8A:
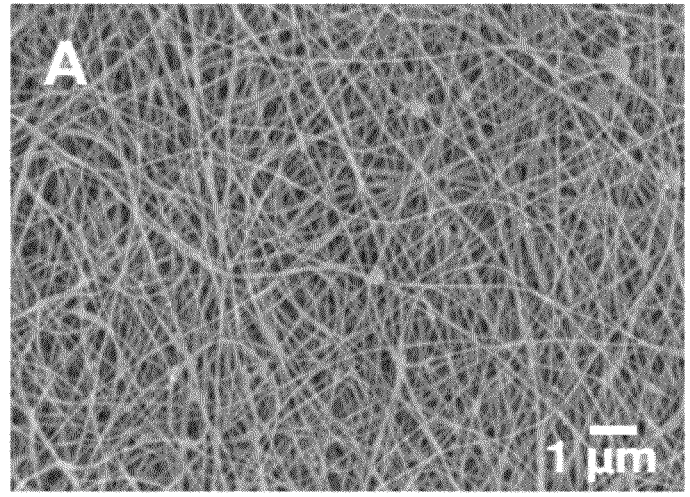
Figure 8B:
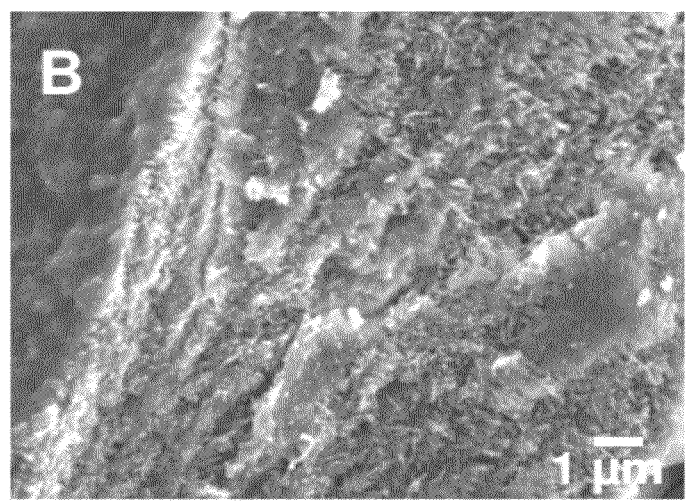
Figure 8C:
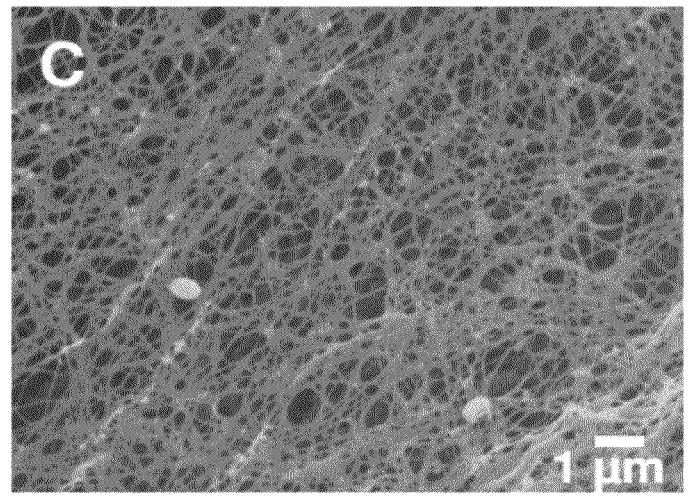
Figure 8D:
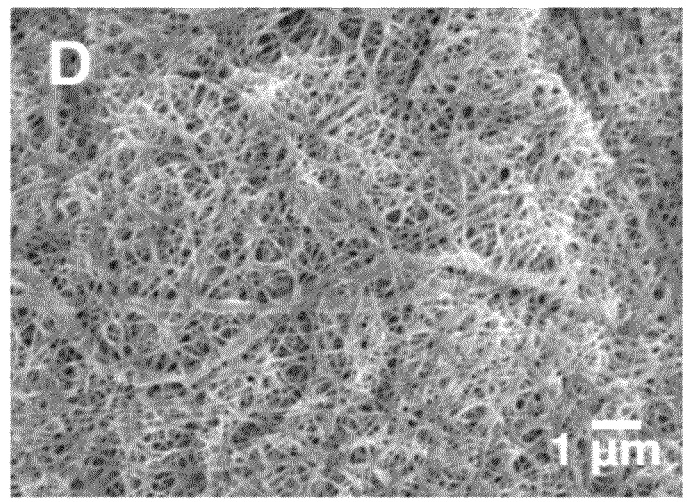

FIGS. 8A and 8B are SEM images of a representative ionically (calcium chloride) crosslinked alginate (alginate/PEO 80:20) fibrous mat of the invention incubated in DI water (FIG. 8A) and SBF (pH 7.4) (FIG. 8B) for seven days at 37° C.

Figure 8E:
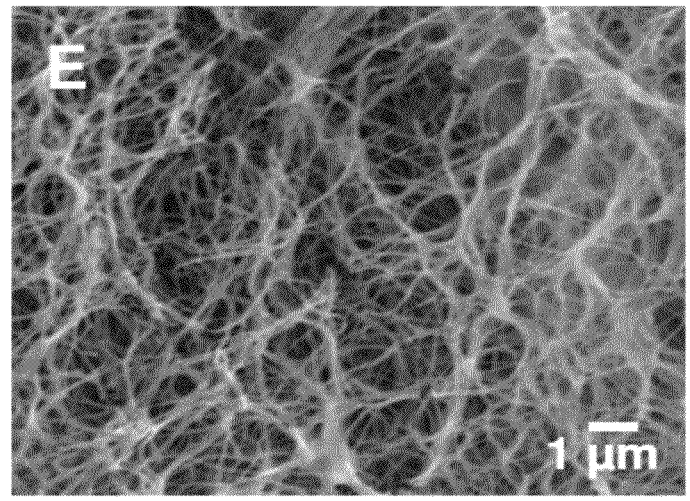
Figure 8F:
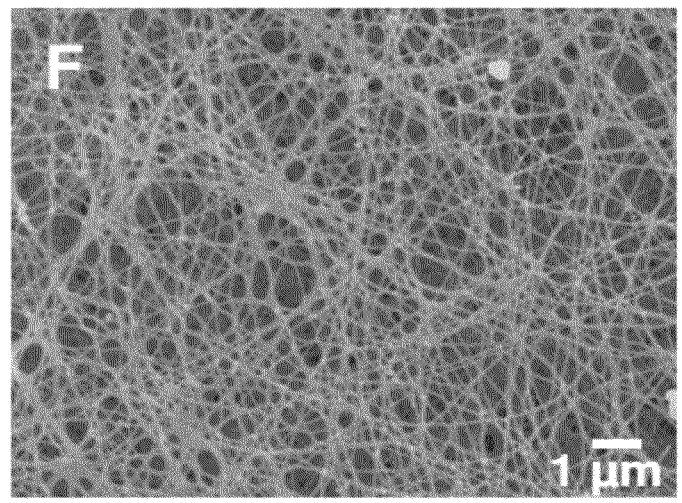

FIGS. 8C-8F are SEM images of representative crosslinked alginate (alginate/PEO 80:20) fibrous mats of the invention incubated in simulated body fluid (SBF) (pH 7.4) for seven days at 37° C.: the fibrous mats were first ionically crosslinked with calcium chloride followed by covalent crosslinking with epichlorohydrin (FIG. 8C), glutaraldehyde (FIG. 8D), hexamethylene diisocyanate (HMDI) (FIG. 8E), or adipic acid hydrazide (ADA) (FIG. 8F).

Figure 9A:
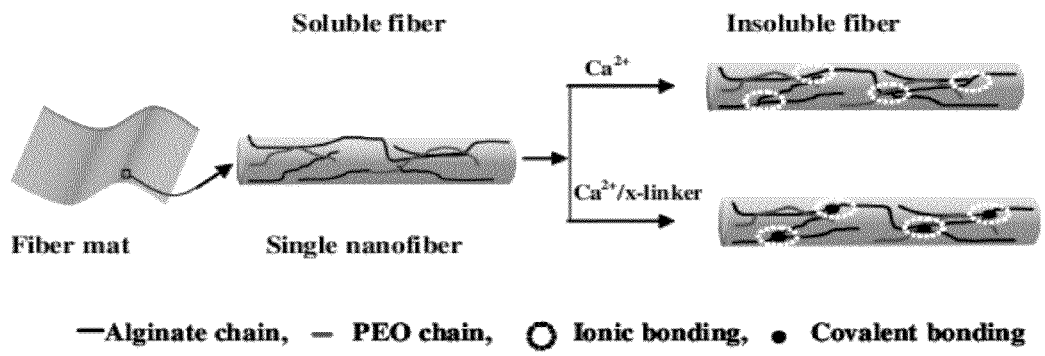

FIG. 9A is a schematic illustration of a process of ionic and covalent crosslinking and depicts the resultant associations between polymer chains in a single nanofiber within a nanofibrous mat after crosslinking.

Figure 9B:
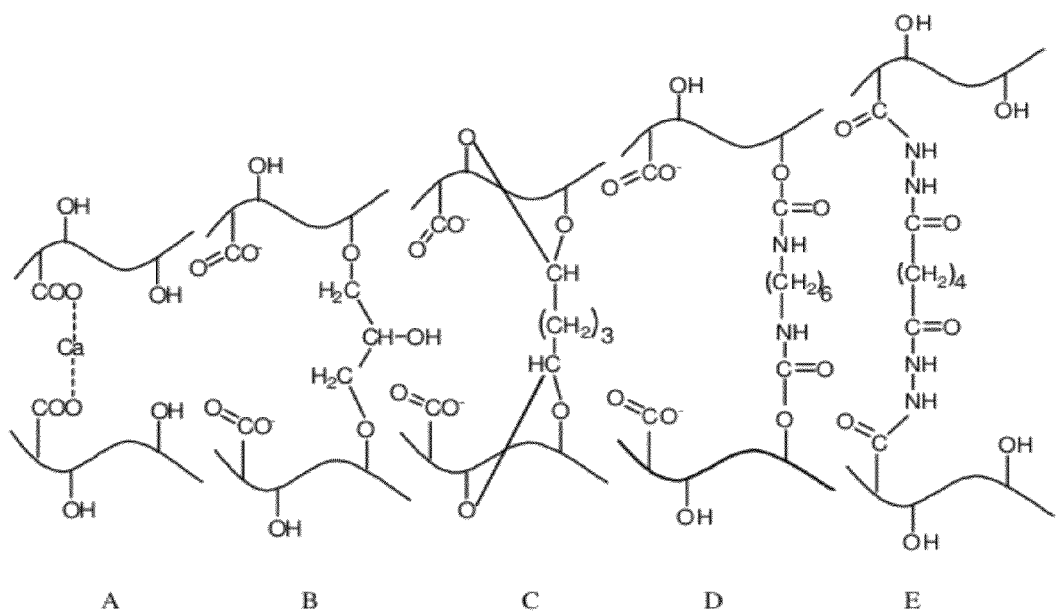

FIG. 9B is a schematic illustration of the chemical structures of crosslinked alginate networks: network structures formed between alginate chains in nanofibers after crosslinking with (A) $CaCl_2$, (B) epichlorohydrin, (C) glutaraldehyde, (D) HMDI, and (E) ADA.

DETAILED DESCRIPTION OF THE INVENTION

The present invention provides alginate-based nanofibers, scaffolds that include nanofibers, implantable devices that include the nanofibers, and methods for making the nanofibers by electrospinning.

In one aspect, the invention provides an alginate-based fiber. As used herein, the term "alginate-based fiber" refers to a fiber that includes alginate. Alginate is a biodegradable polymer derived from seaweed. Alginate can be obtained from, for example, green algae (Chlorophyta), brown algae (Phaeophyta), and red algae (Rhodophyta). Alginate is a linear polysaccharide copolymer that consists of two sterically different repeating units, $(1\rightarrow4)$-$\alpha$-L-guluronate (G unit) and $(1\rightarrow4)$-$\beta$-D-mannuronate (M unit) in varying proportions. Alignate useful in making the fibers of the invention has a mannuronic acid to guluronic acid (MG) ratio of 10 to about 90%. In some embodiments, alignate useful in making the fibers of the invention has a MG ratio of about 50 to 70%. Alignate useful in making the fibers of the invention has a molecular weight of from about 10 kDa to about 1000 kDa. In some embodiments, alignate useful in making the fibers of the invention has a molecular weight of from about 50 kDa to about 500 kDa. Alignate useful in making the fibers of the invention has a viscosity of from about 50 to about 600 cP (2% aqueous solution at 25° C.). In some embodiments, alignate useful in making the fibers of the invention has a viscosity of from about 200 to about 400 cP (2% aqueous solution at 25° C.). Alginate bears structural resemblance to glycosaminoglycan (GAG), one of the major components of the extracellular matrix (ECM) in human tissue.

In one embodiment, the fiber includes from about 30 to about 95 weight percent alginate based on the total weight of the fiber. In one embodiment, about 80 weight percent alginate based on the total weight of the fiber.

In one embodiment, the alginate fiber has a diameter of from about 20 to about 2000 nm. In one embodiment, the fiber has a diameter from about 50 to about 500 nm.

In addition to alginate, the alginate-based fiber of the invention includes a hydrophilic polymer to facilitate production of the fiber by electrospinning. Hydrophilic polymers useful in making the fiber of the invention include poly(alkylene oxide) polymers, polyvinyl alcohol polymers, and polycarboxylic acid polymers. Representative poly(alkylene oxide) polymers include block copolymers (for example, nonionic block copolymers commercially available under the designation PLURONIC and/or POLOXAMER). In one embodiment, the poly(alkylene oxide) polymer is polyethylene oxide. In one embodiment, the hydrophilic polymer (e.g., poly(alkylene oxide)) has a molecular weight of from about 50 kDa to about 1000 kDa. In one embodiment, the fiber includes from about 5 to about 30 weight percent poly(alkylene oxide) based on the total weight of the fiber. In one embodiment, the fiber includes about 20 weight percent poly(alkylene oxide) based on the total weight of the fiber.

To enhance structural integrity, the fibers and scaffolds of the invention can be crosslinked. In one embodiment, the fiber of the invention is crosslinked with an ionic crosslinking agent. Suitable ionic crosslinking agents include a metal ions reactive toward alginate carboxylic acid groups. Representative metal ions include calcium (2), barium (2), strontium (2), copper (2), zinc (2), magnesium (2), manganese (2), cobalt (2), lead (2), iron (3), and aluminum (3) ions.

The fiber of the invention can also be crosslinked with a covalent crosslinking agent. Suitable covalent crosslinking agents include bifunctional crosslinking agents reactive toward alginate hydroxyl and/or carboxylic acid groups. Representative covalent crosslinking agents include carbodiimides, allyl halide oxides, dialdehydes, diamines, and diisocyanates. In certain embodiments, the covalent crosslinking agent is selected from epichlorohydrin, gluteraldehyde, hexamethylene diisocyanate, adipic acid hydrazide, and 1-ethyl-3-(3-dimethylaminopropyl)carbodiimide hydrochloride.

In one embodiment, the fiber of the invention is both ionically crosslinked and covalently crosslinked.

In one embodiment, the fiber of the invention has a Young's modulus of from about 0.004 to about 40 MPa.

In one embodiment, the fiber includes from about 30 to about 95 weight percent alginate and from about 5 to about 70 weight percent polyethylene oxide. In one embodiment, the fiber includes about 80 weight percent alginate and about 20 weight percent polyethylene oxide.

In another aspect of the invention, fibrous scaffolds are provided. The fibrous scaffolds of the invention include a plurality of the fibers of the invention, as described above. The scaffolds of the invention can be manipulated to have shapes and sizes suitable for use as implantable devices.

In one embodiment, the scaffold having a thickness of from about 0.05 to about 5 mm.

The scaffolds can include one or more materials other than the fibers of the invention.

In one embodiment, the scaffold further includes chitosan. In this embodiment, the scaffold includes from about 0.5 to about 15 weight percent chitosan.

In one embodiment, the scaffold further includes collagen. In this embodiment, the scaffold includes from about 0.5 to about 20 weight percent chitosan.

In one embodiment, the scaffold further includes a biologically active amino acid molecule. Representative amino acid molecules include growth factors, fibronectin, laminin, vitronectin, integrins, nucleic acid molecules, lipids, sugars, antisense molecules, anti-inflammatory agents, immunomodulatory agents, molecules that promote cell migration, molecules that promote cell division, molecules that promote cell proliferation and differentiation, molecules that stimulate phenotypic modification of cells, molecules that promote angiogenesis, molecules that promote vascularization, and molecules that promote extracellular matrix disposition.

In one embodiment, the scaffold further includes a signaling ligand. Representative signaling ligands include members of the TGF-β family, bone morphogenic proteins, fibroblast growth factors-1 and -2, platelet-derived growth factor-AA and -BB, and platelet rich plasma and vascular endothelial cell-derived growth factor. In this embodiment, the scaffold includes from about 1 to about 100 ng signaling ligand per gram scaffold.

In a further aspect of the invention, implantable devices are provided. The implantable devices include the fibers and/or the scaffolds of the invention described above. Representative implantable devices include cell transplantation devices, drug delivery devices, wound dressings and hemostats, surgically implantable devices for repairing damaged cartilage in mammalian articulating joints, fabric barriers to hyperplasia and tissue adhesion, vascular prostheses, nerve grafts, spinal fusion cages, and skin substitutes.

In another aspect, the invention provides a method for making the alginate fibers of the invention. In one embodiment, the method includes (a) generating an electrostatic field between a first electrode and a second electrode; and (b) electrospinning an aqueous alginate solution comprising alginate and a hydrophilic polymer onto a collection surface located between the first electrode and the second electrode to provide a plurality of alginate fibers on the collection surface.

In one embodiment of the method, the alginate solution includes from about 1 to about 8 percent by weight alginate. In one embodiment, the alginate solution includes from about 3 to about 5 percent by weight alginate.

In one embodiment, the hydrophilic polymer is selected from a poly(alkylene oxide), a polyvinyl alcohol, and a polycarboxylic acid polymer. In one embodiment, the alginate solution includes from about 1 to about 10 percent by weight poly(alkylene oxide). In one embodiment, the alginate solution includes from about 2 to about 4 percent by weight poly(alkylene oxide). In one embodiment, the poly(alkylene oxide) is polyethylene oxide.

In one embodiment, the ratio of alginate to poly(alkylene oxide) is from about 70:30 to about 95:5. In one embodiment, the ratio of alginate to poly(alkylene oxide) is about 80:20.

In one embodiment, the alginate solution further includes a co-solvent. Suitable co-solvents include polar aprotic solvents. Representative co-solvents include 1,4-dioxane, tetrahydrofuran, acetone, acetonitrile, dimethylformamide, and dimethylsulfoxide. In one embodiment, the co-solvent is dimethylsulfoxide. In one embodiment, the co-solvent is present in the solution in an amount from about 0.5 to about 20 weight percent. In one embodiment, the co-solvent is present in the solution in an amount from about 1 to about 10 weight percent. In one embodiment, the co-solvent is present in the solution in about 5 weight percent.

In one embodiment, the alginate solution further includes a surfactant. Suitable surfactants include nonionic surfactants. Representative surfactants include glycol stearate, cocoamide surfactants, and polyoxyethylene isooctylphenyl ethers (Triton X-100 family). In one embodiment, the surfactant is present in the solution in an amount from about 0.01 to about 1.0 weight percent. In one embodiment, the surfactant is present in the solution in about 0.05 weight percent. In one embodiment, the surfactant is polyoxyethylene(10) isooctylphenyl ether (Triton X-100).

In one embodiment, the alginate solution includes both a co-solvent and a surfactant, as described above.

In one embodiment, the zero shear viscosity of the alginate solution is from about 2.0 to about 8.0 Pa·s.

In one embodiment, the method further includes treating the plurality of alginate fibers with an ionic crosslinking agent to provide a plurality of ionically crosslinked alginate fibers. Suitable ionic crosslinking agents are described above and include metal ions, such as calcium (2) ion, barium (2) ion, strontium (2), copper (2), zinc (2), magnesium (2), manganese (2), cobalt (2), lead (2), iron (3), and aluminum (3) ions.

In one embodiment, the method further includes treating the plurality of ionically crosslinked alginate fibers with a covalent crosslinking agent to provide a plurality of covalently crosslinked alginate fibers. Suitable covalent crosslinking agents are described above and include carbodiimides, allyl halide oxides, dialdehydes, diamines, and diisocyanates.

The fibers of the invention can be crosslinked ionically, covalently, or ionically and covalently. In one embodiment, the method of the invention includes treating the alginate fibers with a covalent crosslinking agent to provide a plurality of covalently crosslinked alginate fibers.

Details of the alginate fibers of the invention, their properties, and methods for their preparation are described below.

The present invention provides a method for fabrication of alginate-based nanofibers using electrospinning. Although electrospinning has proven to be an effective way of generating nanofibrous structures for many materials, fabrication of alginate nanofibers by electrospinning is challenging. This is because the gelation of alginate solution starts to occur at very low polymer concentrations (e.g., about 2 wt. % for alginate in deionized (DI) water). At such a low concentration, the solution contains insufficient material to generate fibrous structures, and, rather, sprayed droplets or a structure with short fibers embedded with beads is obtained. At slightly higher polymer concentrations, the solution becomes so viscous that it cannot be injected.

In the method of the invention, this problem is solved by the incorporation of a fraction of copolymer, and to apply one or more surfactants or/and one or more cosolvents to the alginate solution. The underlying principle is to control the sol-gel transition by using additives, which interact with the alginate solution to reduce the solution's viscosity, so that gelation can occur at a higher polymer concentration.

In one embodiment, the copolymer useful in the method of the invention is polyethylene oxide (PEO), a biocompatible and biodegradable polymer. PEO is a non-ionic polymer that is soluble in water, and interacts with alginate through hydrogen bonding, reducing the viscosity of the alginate solution. In one embodiment, alginate-PEO solutions were prepared by mixing alginate and PEO in DI water, both at a fixed concentration of 4 wt. %. Solutions with alginate/PEO ratios in the range 40:60-90:10 were prepared.

The instrumentation set-up for electrospinning alginate solutions was similar to that reported previously (N. Bhattarai, D. Edmondson, O. Veiseh, F. A. Matsen, M. Q. Zhang, *Biomaterials* 26:6176, 2005). The distance between two electrodes, that is, the distance between the solution-injection tip and the fiber-collecting cylinder, was set to 20 cm. A voltage of 15 kV was applied between the electrodes. Experimental results have shown that solutions with lower alginate/PEO ratios had better electrospinnability, and stable, completely "bead-free" nanofibers were obtained at an alginate/PEO ratio of 50:50 or below. As used herein, the term "electrospinnability" of a solution refers to the ease with which electrospun fibers free from nonfibrous structures (sprayed droplets, fibers embedded with beads) are produced. To obtain alginate nanofibers at a higher alginate/PEO ratio, which is desirable for some tissue-engineering applications, an amount of a surfactant (e.g., non-ionic surfactant such as polyoxyethylene (10) isooctylphenyl ether, commercially available under the designation Triton X-100) and/or a co-solvent (e.g., dimethyl sulfoxide (DMSO)) were introduced into the polymer solution. Continuous nanofibers with alginate/PEO ratios in the range 70:30-90:10 were generated at typical concentrations of 0.5 wt. % Triton X-100 and 5 wt. % DMSO.

Figure 1A:
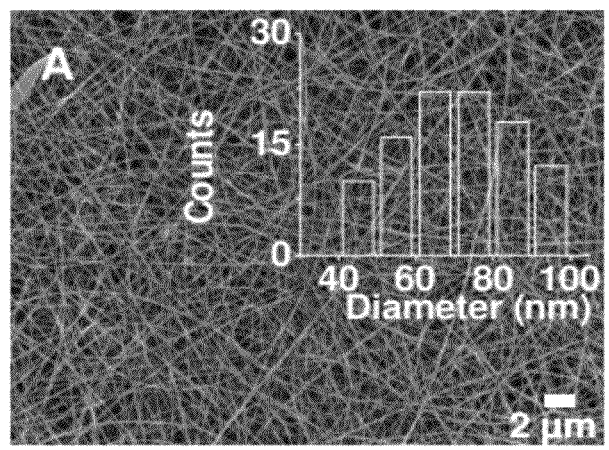
FIGS. 1A-1C' are scanning electron microscope (SEM) images of representative alginate-polyethylene oxide (PEO) fibers of the invention electrospun from alginate/PEO solutions containing 0.5 wt % Triton X-100 surfactant and 5 wt % DMSO co-solvent.
Figure 1A:
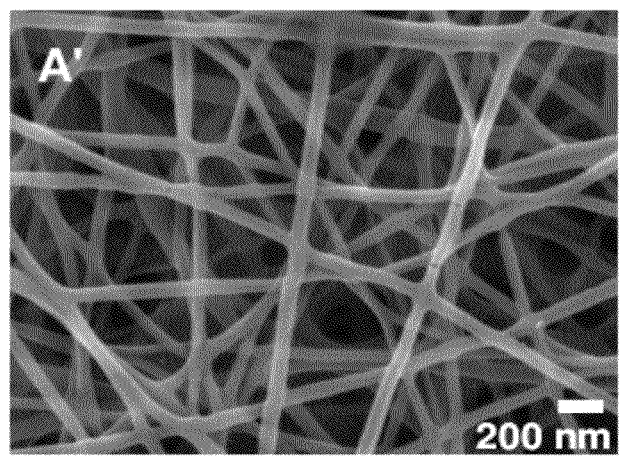

FIGS. 1A, 1A', 1B, 1B', 1C, and 1C' are scanning electron microscopy (SEM) images of nanofibers spun from solutions with three different alginate/PEO ratios, and the insets display the corresponding fiber size distributions. Solutions with alginate/PEO ratios in the range 70:30-80:20 yielded cylindrical nanofibers with a mean diameter of approximately 75 nm and a relatively narrow size distribution. The nanofibers spun from the solution with an alginate/PEO ratio of 90:10 resulted in a relatively poor fiber size distribution.

Nanofibers spun from a solution with an alginate/PEO ratio of 80:20 exhibited the most favorable morphology, while retaining a high alginate/PEO ratio, and, thus, these fibers were further studied for their structural integrity, mechanical properties, and cellular compatibility. The choice of chondrocytes as target cells for this initial demonstration of cellular compatibility of alginate-based nanofibers was motivated by the inability of damaged articular cartilage to self-heal or be functionally restored, and the fact that the alginate material has been demonstrated to promote cartilage regeneration. The ECM of articular cartilage primarily consists of type II collagen and GAGs. Collagen and GAGs form a strong, porous, fibrous composite material. The collagen gives tensile strength to the cartilage, whereas the GAG imparts elasticity. GAGs are considered to play a key role in modulating chondrocyte cell morphology, differentiation, and function.

Figure 2A:
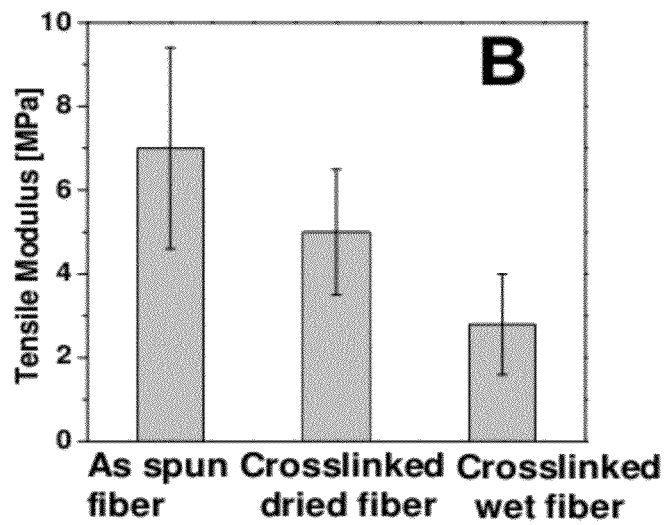
FIG. 2A is a bar graph comparing the tensile moduli of representative alginate-PEO fibers of the invention electrospun from an 80:20 alginate/PEO solution: as spun fiber; calcium chloride crosslinked dried fiber; and calcium chloride crosslinked wet fiber.

Stiffness, or modulus, is a physical material property to be considered for applications in regenerative medicine and tissue engineering. In most cases, it is preferable to have the material's modulus close to that of the target tissue to avoid possible stress-shielding effects and maintain sufficient mechanical support during in vitro and/or in vivo cell growth and tissue-remodeling processes. Young's moduli of representative dried alginate-PEO nanofibers with and without calcium chloride crosslinkage are 5±1 MPa and 7±2 MPa, respectively, while a wet nanofiber crosslinked with calcium chloride has a modulus of 2.8±1.2 MPa (FIG. 2A). These values are comparable to those of human articular cartilage (1-10 MPa) and the equilibrium tensile modulus of bovine articular cartilage (2-7 MPa).

Figure 2B:
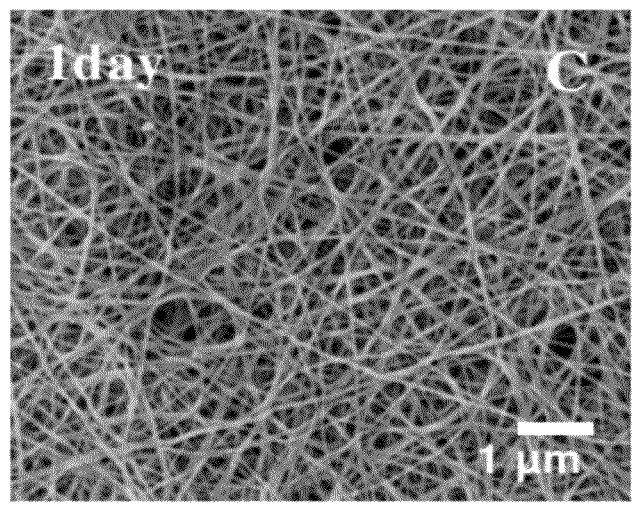
FIGS. 2B and 2C are scanning electron microscope (SEM) images of representative alginate-polyethylene oxide (PEO)
Figure 2C:
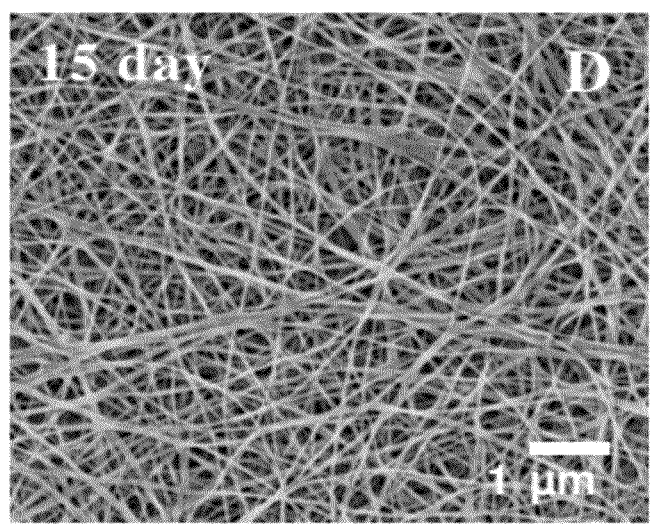

For both in vitro and in vivo applications, materials are expected to maintain their structural integrity in an aqueous environment. The structural integrity of alginate-based nanofibers in an aqueous environment has been examined by immersing alginate-PEO nanofibers in deionized (DI) water for up to 15 days. SEM images of the nanofibers at day one and day fifteen are shown in FIGS. 2B and 2C, respectively. No apparent change in fiber morphology was observed, and the nanofibrous structure was retained.

For the target tissue, cartilage chondrocyte-like cells (HTB-94) were used to evaluate the cellular compatibility of alginate nanofibers. FIGS. 3A and 3B show the SEM images of chondrocyte cells cultured on the alginate-PEO nanofibers in Dulbecco's modified eagle medium (DMEM) for 72 h. The cells attached well and formed cell clusters on the nanofibrous structure. The cells appeared round in shape and maintained their characteristic phenotypes. A round cellular morphology is indicative of the characteristic function of chondrocytes, resulting from the organization of sparse active filaments. Cell viability was assessed using a Live/Dead Assay Kit (Molecular Probes). The fluorescence microscopy image of both live and dead cells on the nanofibrous scaffold incubated with chondrocyte cells for 72 hours is shown in FIG. 3C. The live cells appear as bright spots, and the dead cells are too few to be seen in the figure. The cellular viability, which is defined as the number of live cells divided by the total number of cells (live cells plus dead cells), was determined to be approximately 95%. Notably, unlike bulk alginate scaffolds, which usually require precoated adhesion proteins such as fibronectin or arginine-glycine-aspatic acid peptides to facilitate cell adhesion, the alginate-based nanofibrous matrix does not need such pretreatment. The underlying mechanism for such an enhancement in cell adhesion is not clear, but the large specific surface areas of nanofibers that provide a high density of cellular binding sites, are thought to be one of the major factors for the enhanced cellular activities.

Electrospinning of Alginate Solutions.

Alginate solutions made by dissolving alginate in DI water at a concentration of 2 wt % or below do not generate a fibrous structure at any input voltage on electrospinning. Instead, the solutions yielded droplets or leaked out from the injection tip. Increasing the alginate concentration from 2 to 5 wt % caused the solution to become highly viscous, which impeded its continuous flow through the capillary tip, rendering the solution unspinnable. Studies have shown that it is difficult, if not impossible, to produce nanofibers from aqueous solutions of pure natural polymers. In the method of the invention, alginate solutions are blended with a miscible hydrophilic synthetic polymers having neutral charge (e.g., PEO). The hydrogen bonding between these hydrophilic polymers and natural polysaccharides is responsible for the miscibility and improved properties of the blends solutions. To make alginate solution spinnable, PEO was used as the supporting polymer.

Aqueous solutions of pure PEO are readily electrospinnable at a wide range of concentrations. Alginate solutions (4 wt %) can be prepared at ambient conditions and so can PEO solutions at the concentration.

In one embodiment, the alginate solution is a blend solution of alginate/PEO at a final polymer concentration of 4 wt %. Blend solutions with varying ratios of alginate to PEO from 40/60 to 90/10 were prepared by mixing a 4 wt % alginate solution with a 4 wt % PEO solution at different proportions. As mentioned above, a 4 wt % pure alginate solution is too viscous to be spinnable. Upon introducing PEO solution into the alginate solution, the viscosity of the resultant solution was reduced, and electrospinning the solution yielded fibrous structures, suggesting that solution viscosity is one of determinants that regulate the electrospinnability and the structures of produced nanofibers. To quantify the effect of solution viscosity on the electrospun fiber structure, the shear viscosity of the blend solutions as a function of PEO/alginate ratio and shear rate was measured, and the electrospun products from these solutions were studied with SEM.

FIG. 4 is a graph comparing shear viscosities of polymer solutions having different alginate/PEO weight ratios (100:0; 90:10; 80:20; and 60:40) as a function of shear rate. FIG. 4 shows that the viscosity of the blend polymer solution decreased monotonically with increasing PEO content. The SEM images of the as-spun products of alginate solutions are presented in FIG. 5. FIGS. 5A-5D are SEM images of electrospun structures from alginate solutions having alginate/PEO ratios of 90:10; 80:20; 70:30; and 60:40, respectively. FIG. 5 shows that the as-spun products changed progressively from droplets, a structure of beads with short fibers, to a fibrous structure as the PEO/alginate ratio increased, corresponding to the decrease in solution viscosity shown in FIG. 4. Completely "bead-free" nanofibers were obtained at a PEO/alginate ratio equal to or greater than 50%.

The high viscosity of a pure alginate solution is believed primarily due to strong intermolecular interaction between polymer chains and possible entanglements that act as knots (i.e., the physical junctions of alginate gels). The decrease in viscosity by addition of PEO can be attributed to the changes in inter- and intra-molecular interactions of alginate chains. The introduced PEO acts as polybase and has strong tendency to form interpolymer complex with polycarboxylic acids. The interpolymer complexes have a compact structure, so that the hydrodynamic volume of the complex is smaller than the volume sum of individual macromolecules. Therefore, the complexation of two polymers in solution leads to a decrease in viscosity. The addition of PEO molecules into the polyanionic alginate solution creates interpolymer complexes by forming hydrogen bonds between hydrogen on hydroxyl/carboxyl groups of alginate and ether oxygen on PEO, which disrupts the associative structure of alginate chains.

Both PEO and alginate are biocompatible and biodegradable polymers and have been used in a variety of tissue engineering applications. However, natural polymers are generally preferable in regenerative medicine. It is therefore advantageous to produce an alginate fiber product that has the alginate component as great as possible in produced nanofibers while maintaining a uniform fibrous. As illustrated in FIGS. 4 and 5, more uniform nanofibrous structures are achieved at an alginate/PEO ratio less than about 60/40.

To reduce the alginate solution viscosity while maintaining a high alginate/PEO ratio, in one embodiment, the alginate solution includes a nonionic surfactant.

Figure 5A:
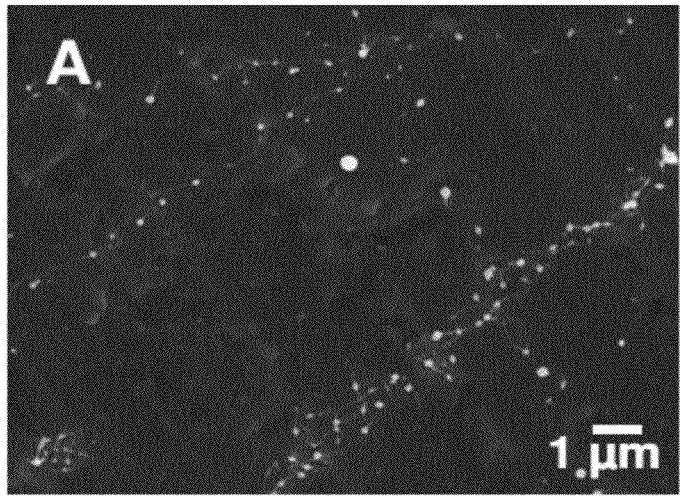
Figure 5B:
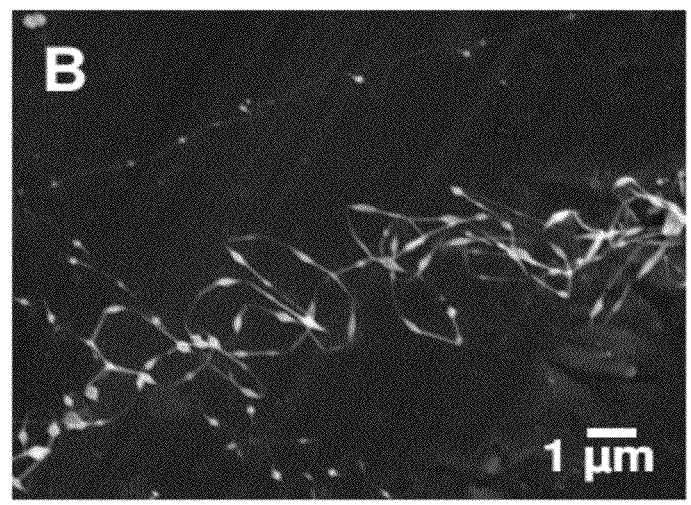
Figure 5C:
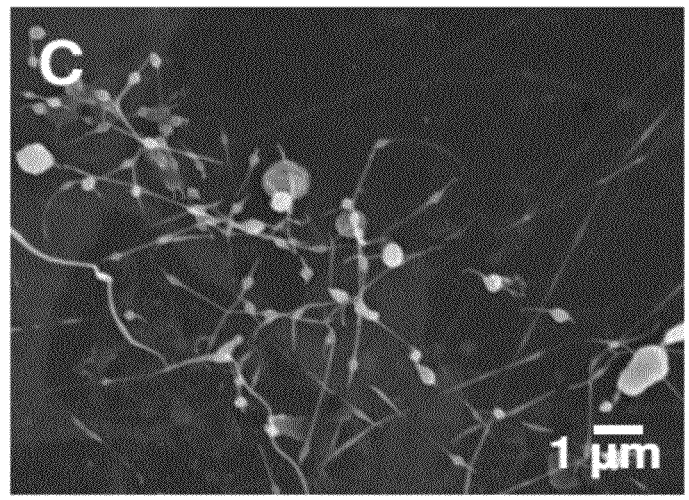
Figure 5D:
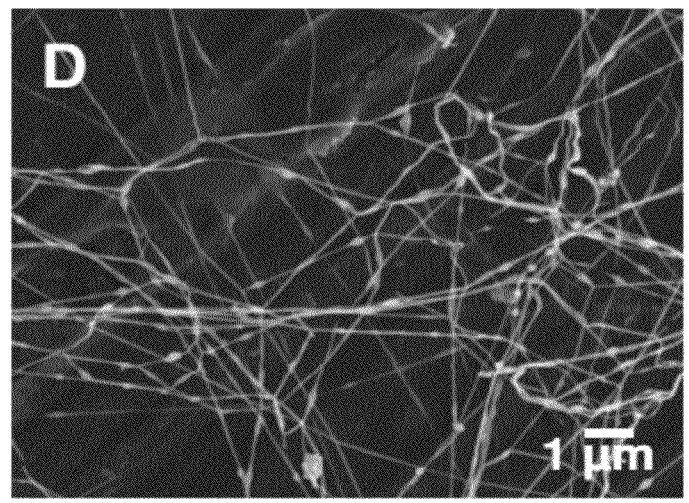

FIGS. 6A-6D are images of the electrospun structures when 0.5 wt % nonionic surfactant (Triton X-100) was introduced in 4 wt % solution of alginate/PEO (80/20). The addition of the surfactant substantially improved the fibrous structure compared to the solution with the same alginate/PEO ratio without the surfactant (FIG. 5B). However, the as-spun structure was not exclusively fibrous and "beads" were seen embedded in the fibers. To further improve the electrospun structure, a co-solvent (DMSO) was introduced into the solution. A bead-free, uniform fibrous structure was produced by addition of surfactant (0.5 wt % Triton X-100) and co-solvent (5 wt % DMSO). The resultant structures are shown in FIGS. 6B-6D (differing magnifications). By the method, solid, cylindrical nanofibers with a main diameter of about 75 nm were obtained and no phase separation between alginate and PEO was observed.

FIGS. 6A-6D are images of electrospun alginate/PEO fibers from 80:20 alginate/PEO solutions: FIG. 6A is a SEM image of fibers obtained by adding Triton X-100 (0.5 wt %); FIG. 6B is a SEM image of fibers obtained by adding Triton X-100 (0.5 wt %) and DMSO (5.0 wt %); FIG. 6C is a transmission electron microscope (TEM) image of the fibers of FIG. 6B; and FIG. 6D is a higher magnification TEM image of the fibers of FIG. 6B.

Triton X-100, a nonionic surfactant, is structurally similar to PEO, bearing short chain of ethylene oxide repeating units in its hydrophilic long tail. The surfactant dissolves readily in aqueous solution and interacts with alginate in a fashion similar to those between alginate and PEO. When DMSO was used as the co-solvent, a dipole-dipole interaction was introduced between alginate chains and DMSO because DMSO has a large dipole moment (i.e., 3.96). This interaction weakened the association between alginate chains and improved the solution spinnability. As demonstrated, the combination of a co-solvent (e.g., DMSO) and a nonionic surfactant (e.g., Triton X-100) afforded significant processing advantages to modulate the alginate solution at high alginate/PEO ratios. The incorporation of small amounts of Triton X-100 and DMSO into alginate/PEO solutions has no effect on the chemistry of the final fibrous product because both are readily soluble in water and can be easily removed from nanofibers during the washing or crosslinking of the nanofibers. Additionally, as a co-solvent, most of the DMSO evaporates during the electrospinning as the solution jet travels from the injection tip to the collector.

Effect of Solution Viscosity and Stability on the Formation of Nanofibers.

The properties of alginate solutions appear to change during storage over time in the ambient environment. Solution viscosity plays an important role in electrospinnability of polymer solutions and the structures of resultant polymer fibers.

Freshly prepared alginate/PEO solution were observed to be difficult to process. However, when the solution was left in the ambient environment for certain time, the solution became more spinnable. Therefore, it is believed that the underlying mechanism for this observation provides insight into electrospinnability of the polymer solutions. Spinnability appears to be directly related to solution viscosity. To determine whether the viscosity of an alginate polymer solution would change over time at ambient conditions, a 4 wt % alginate solution was maintained at room temperature over a period of 30 days and measuring the viscosity of the solution at different time points. As shown in FIG. 7A, the viscosity of the solution dropped considerably in the first two weeks and gradually saturated thereafter. The viscosity drop with the storage time was believed attributable to a decrease in the average molecular weight of alginate as a result of polymer chain degradation. Alginate molecular chain scission was caused by the breakage of glycosidic bonds due to aqueous hydrolysis. Chain scission was confirmed by maintaining an alginate solution in the ambient environment and then sampling the solution at different storage times and characterizing the samples by FTIR and UV spectroscopy. FIG. 7B shows the FTIR spectra of these samples, with the spectrum of as-received alginate powder (as control) shown for comparison. Peaks of sodium alginate at 3400, 1610 and 1089 $cm^{-1}$ are attributed to —OH, C—O—O$^-$, C—O—C groups, respectively. The breakage of glycosidic bonds leads to the formation of more hydroxyl groups, which is characterized by a sharp increase in the intensity of the hydroxyl group peak at 3400 $cm^{-1}$ over storage time as compared to the broad and weak absorbance of the as-received alginate. The increased peak intensities of C—O—C and C—O—O$^-$ groups are also as expected as shown in FIG. 7B. The alginate polymer chain degradation was further confirmed by UV spectrometry and the results are shown in FIG. 7C. The UV absorption band was shifted from 225 nm at day 0 to 240 nm at day 15 and the intensity of the absorbance increased with solution storage time. The peak shift and increase in absorbance are due to the double bonds formed upon a polymer main chain scission creating a ring opening, as also observed in radiation induced degradation of alginate. The time-dependent changes in both FTIR and UV spectra correspond well to the change in solution viscosity: the most significant changes in the spectra occurred in the first two weeks as the solution viscosity (see FIG. 7A). FIG. 7A is a graph illustrating zero shear viscosity of a 4 wt % alginate solution as a function of storage time. FIG. 7B compares the infrared (FTIR) spectra of the 4 wt % alginate solution as a function of storage time (Day 6, 10, 15, 20, and 30) to the infrared spectrum of as-received alginate powder (Control). FIG. 7C compares the ultraviolet (UV) absorbance spectra of the 4 wt % alginate solution as a function of storage time (Day 6, 10, 15, 20, and 30) to the absorbance spectrum of as-received alginate powder (Control).

The influence of solution storage time on electrospun product was evaluated. Alginate solutions were maintained in the ambient environment for different times were mixed with PEO solutions to prepare blend solutions with an alginate/PEO ratio of 80/20. These blend solutions were then electrospun immediately after preparation and the resultant structures were examined by SEM. The study revealed that alginate solutions subjected to different storage times can be divided into three regions in term of viscosity as shown in FIG. 7A, with the solutions that fall in the same region producing similar fiber morphology. FIGS. 7D-7F show representative images of the electrospun fibrous structure for each region (alginate solutions stored for 2, 5 and 15 days). FIGS. 7D-7F are SEM images of fibers electrospun from alginate solutions having viscosities in Regions I, II, and III, respectively, of FIG. 7A.

These results further demonstrated a strong correlation between solution viscosity and electrospun structure. Solutions having viscosities that fall in Region II produced desired uniform nanofibrous structures. Solutions stored for prolonged time beyond 15 days had too low viscosity (Region III) and yielded "bead-string" structures. The solution storage time also affected the electrospinning rate. The electrospinning rate was measured by solution volume consumption in unit time. For solutions stored for 2, 5 and 15 days the rates were found to be 0.5±0.15, 5.0±0.8 and 15.0±2.5 ml/h, respectively.

A practical implication of this finding is that as-received alginate is not necessarily suitable for fabrication of nanofibers by electrospinning even if the polymer has been demonstrated to be spinnable. Thus, the solution viscosity rather than storage time may be taken as a practical indicator to identify the spinnability of a particular polymer. Changing molecular weight through storage or a "natural" course is not a recommended approach to reduce solution viscosity.

Integrity of Nanofibrous Structure in Aqueous Media.

Alginate and PEO are soluble in aqueous medium. Most tissue engineering applications require materials to maintain structural integrity in aqueous environments (e.g., cell culture medium, human body) for prolonged periods. This is particularly important for nanofeatured materials as they degrade more quickly than bulk materials. One way to improve the stability of hydrophilic polymeric materials in solution is to crosslink the materials. Crosslinking may be applied to each fiber component (alginate and PEO). In one embodiment, the fibers are crosslinked by alginate crosslinking alginate. Alginate crosslinked with ionic crosslinking agents are stable in water, but unstable in solutions containing salt ions. For both in vitro and in vivo applications, materials are often exposed to aqueous media with different ionic strengths. In this case, covalent crosslinking of nanofibers may prove be a better solution. However, covalent crosslinking of alginate nanofibers needs to proceed in aqueous solution, a process that itself may degrade alginate nanofibers within the reaction time frame. In one embodiment of the method of the invention, the fibers are first ionically crosslinked and then covalently crosslinked.

For ionic crosslinking, nanofibrous mats were soaked with ethanol and then with saturated solution of calcium chloride ($CaCl_2$) in 75% ethanol, followed by incubation in aqueous $CaCl_2$ solution. The structural stability of the ionically crosslinked nanofibrous mats was examined by incubation in DI water and SBF. FIGS. 8A and 8B are SEM images of a representative ionically (calcium chloride) crosslinked alginate (alginate/PEO 80:20) fibrous mat of the invention incubated in DI water (FIG. 8A) and SBF (FIG. 8B) for seven days at 37° C. FIG. 8A shows that the ionically crosslinked alginate fibrous mat remained intact in water, whereas FIG. 8B shows that the mat completely lost its initial nanofibrous structure. A similar result as in SBF was obtained for the mat incubated in PBS.

The crosslinking of alginate based nanofibers with bivalent metal ions such as $Ca^{2+}$, $Ba^{2+}$, $Sr^{2+}$ is via electrostatic interaction of two carboxyl groups on different alginate chains, in which the polymeric molecule loses its freedom of movement and a crosslinked network structure is formed. The crosslinked alginate structure is stable in water in a temperature range of 0-100° C. However, when placed in SBF, which contains salt ions $Na^+$, the dissolution of the nanofiber mat occurs as a result of the exchange of $Na^+$ ions in the solution with $Ca^{2+}$ ions bound to carboxylates in alginate chains. For cell culture medium, this may be less problematic, because the ionic salt concentration in in-vitro cell culture medium is maintained at a level lower than in SBF and PBS where the ion exchange rate is low and the nanofibrous structure can survive prolonged culture time.

In order to retain structural integrity of alginate based nanofibrous mats in aqueous media of a wide range of ionic strengths, the nanofibrous mats crosslinked with $CaCl_2$ were further covalently crosslinked. Covalent crosslinking of alginate is possible because alginate has two active functional groups (i.e., hydroxyl and carboxylate). Four representative homobifunctional crosslinking agents were used to crosslink the alginate fibers: (1) epichlorohydrin, (2) glutaraldehyde, (3) hexamethylene diisocyanate (HMDI), and (4) adipic acid hydrazide (ADA). Each of these crosslinking agents is used to crosslink polymers bearing hydroxyl and carboxylic functional groups to render water-soluble polymers water insoluble.

FIGS. 8C-8F are SEM images of representative crosslinked alginate (alginate/PEO 80:20) fibrous mats of the invention incubated in SBF (pH 7.4) for seven days at 37° C.: the fibrous mats were first ionically crosslinked with calcium chloride followed by covalent crosslinking with epichlorohydrin (FIG. 8C), glutaraldehyde (FIG. 8D), hexamethylene diisocyanate (HMDI) (FIG. 8E), or adipic acid hydrazide (ADA) (FIG. 8F).

The process of ionic and covalent crosslinking, as well as the resultant associations between polymer chains in a single nanofiber within a nanofibrous mat after crosslinking is illustrated schematically in FIG. 9A. The chemical structures of the resultant crosslinked networks are illustrated schematically in FIG. 9B; molecular network structures formed between alginate chains in nanofibers after crosslinking with (A) $CaCl_2$, (B) epichlorohydrin, (C) glutaraldehyde, (D) HMDI, and (E) ADA. The covalent crosslinking of alginate nanofibers occurs by the formation of inter- and intra-molecular covalent bonds between alginate chains in the nanofiber as well as at fiber/fiber overlap junctions. Epichlorohydrin, glutaraldehyde, and HMDI utilize the hydroxyl groups of alginate, whereas ADA utilizes carboxyl groups. Covalently crosslinked nanofibrous mats were characterized by dissolution test in PBS. FIGS. 8C-8F show SEM images of nanofibrous mats crosslinked with epichlorohydrin, glutaraldehyde, HMDI, and ADA, respectively, after incubated in SBF for one week.

In contrast to ionically crosslinked nanofibrous mats (e.g., FIG. 5B), the mats after dual crosslinking (i.e., both ionic and covalent) retained their fibrous structures, although changes of different degrees in fiber morphology (swelling or melting) were observed except for the fibers crosslinked with ADA which showed no evident change.

Because the solubility of epichlorohydrin in water is relatively poor, the epichlorohydrin crosslinking reaction was conducted in 50% ethanol. To promote the reaction of epichlorohydrin with hydroxyl groups of alginate, the pH of the reaction mixture was maintained basic by addition of dilute NaOH solution. For crosslinking alginate nanofibers using glutaraldehyde, the reaction was carried out in 50% ethanol and catalyzed with dilute HCl to facilitate the reaction between aldehyde and the hydroxyl groups. The observed fiber swelling and melted fiber junctions in PBS after crosslinking is common for hydrophilic biopolymers when they are incubated in aqueous medium. Additionally, both epichlorohydrin and glutaraldehyde crosslinking reactions occurred at highly basic or acidic solutions, which may potentially damage the fine structures of the nanofibrous mats during the crosslinking. Crosslinking alginate nanofibers with HMDI in DMSO/DMF mixture avoids the use of aqueous solution. However, the resultant nanofibrous mat exhibited relatively poor morphology in PBS and some of the nanofibers appeared dissolved after one week of incubation (FIG. 8E). This is likely due to less efficient crosslinking as a result of the poor solubility of alginate in DMSO/DMF mixture. The ADA crosslinking was carried out in MES aqueous solution at mild pH and the reaction time was relatively short. This approach yielded the best retained fibrous structure in PBS (FIG. 8F) and used no organic solvents for crosslinking, which is more favorable for a majority of tissue engineering applications.

The crosslinking of representative alginate fibrous mats of the invention is described in Example 2.

The alginate fibers of the invention are fabricated by electrospinning. Polymer solution viscosity was a key factor that regulates the spinnability and the structure of the electrospun product. Solutions having certain ranges of viscosity produce fibrous structures. Solution viscosity can be changed in a number of ways including addition of a second hydrophilic polymer and/or surfactants or alteration of polymer molecule weight. Alginate molecular structure in solution and thus the solution viscosity changes over time even in the ambient environment resulting in inconsistent structural properties in polymeric nanofibrous material production, as nanofeatured materials are particularly susceptible to changes in molecular structure, environmental conditions (e.g., heat or radiation), and experimental parameters. Polymer solution viscosity serves a practical indicator to identify the spinnability of a polymer solution and differentiate the structures of electrospun products.

For tissue engineering applications, a scaffolding material must retain its structural integrity during time of service (from days to months depending on application) in designated biological environments which can be in vitro or in vivo. The crosslinked alginate fibers of the invention improve the stability of alginate based nanofibers in different chemical or biological environments.

The following examples are provided for the purpose of illustrating, not limiting, the invention.

EXAMPLES

Example 1

The Preparation and Characterization of Representative Alginate Fibers

In this example, the preparation and characterization of representative alginate fibers of the invention, alginate-PEO fibers, is described.

Materials.

Alginic acid sodium salt from brown algae with medium viscosity and PEO (weight-average molecular weight (Mw) 900 kDa) were purchased from Sigma-Aldrich. Triton X-100 was purchased from VWR. A human chondrocyte-like cell line (HTB-94) was obtained from American Type Culture Collection (Manassas, Va.). All culture media and reagents were purchased from Invitrogen Life Technologies. Two different buffers, phosphate-buffered saline (PBS) and simulated body fluid (SBF), were prepared in the lab using buffer constituents from Sigma and J.T. Baker Chemical Co.

Electrospinning of Nanofibers.

4 wt % alginate solutions and 4 wt % PEO solutions were prepared separately by dissolving alginate or PEO in DI water, followed by centrifugation to remove air bubbles. The alginate and PEO solutions of different proportions were then mixed to obtain mixtures with weight ratios of alginate to PEO in the range 40:60-90:10, and the resultant mixtures were stirred for 3 h. Solutions containing 0-1.0 wt. % Triton X-100 and 0-10 wt. % DMSO were mixed with alginate-PEO solutions, and the mixtures were stirred for an additional 3 h and centrifuged to remove air bubbles before use in electrospinning. The electrospinning system was similar to that reported previously (N. Bhattarai, D. Edmondson, O. Veiseh, F. A. Matsen, M. Q. Zhang, *Biomaterials* 26:6176, 2005). Briefly, a DC voltage of 10-15 kV with low current output (High DC power supply, Del Electronics Corp.) was applied between the syringe tip and a cylindrical collector. The typical distance between the syringe tip and the grounded collector was 17-20 cm. Polymer solution inside the syringe was charged with a positive voltage by dipping a platinum wire into the solution from a positive lead; the cylindrical collector was grounded.

Characterization of the Nanofibrous Structure.

The electrospun nanofibers were collected as a fibrous mat from the collector. The nanofibrous structure was crosslinked with $CaCl_2$ solution at room temperature. The nanofibrous mat was soaked in 95% ethanol for 5 min and rinsed with 1 wt. % $CaCl_2$ solution in ethanol for 10 min. The ethanol/$CaCl_2$-treated fiber mat was incubated with a $CaCl_2$ solution for 1 h. The nanofibrous mat was then immersed in DI water for 1 h and rinsed with DI water to remove excess $CaCl_2$. Samples were dried at room temperature after washing with absolute ethanol. To examine the integrity of the nanofibers, the nanofibrous mat was immersed in DI water at room temperature for specified time periods. The morphology of the nanofibrous structure was examined using scanning electron microscopy (SEM) (JEOL JSM-7000) at an accelerating voltage of 10 kV after sputter-coating the specimens with Au—Pd. The average diameter of the electrospun nanofibers was determined by measuring the diameters of the nanofibers at 100 different points in a 645×484 SEM image.

Figure 1B:
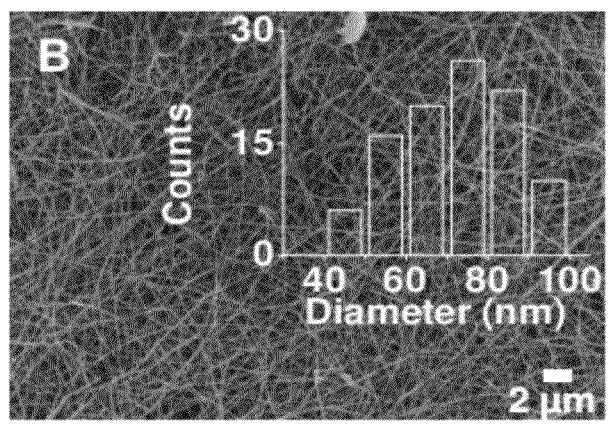
Figure 1B:
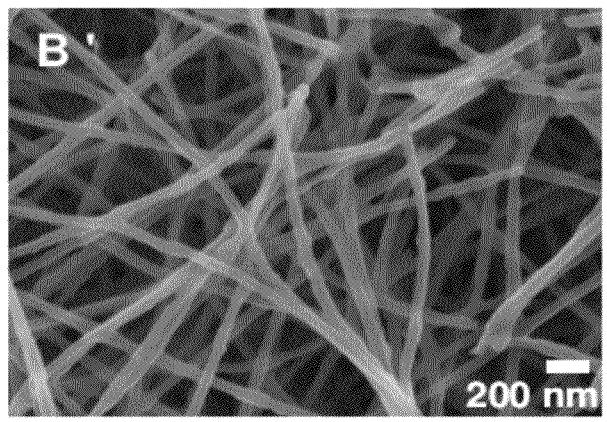
Figure 1C:
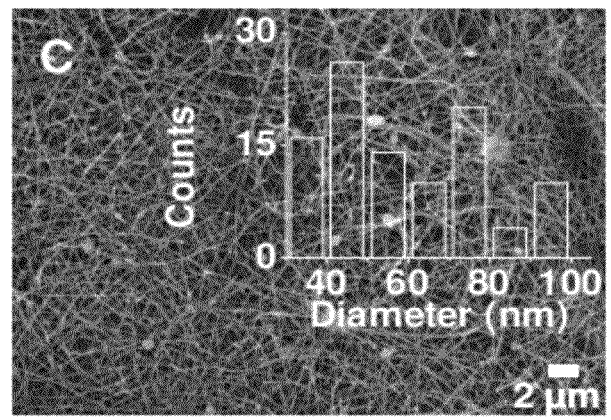
Figure 1C:
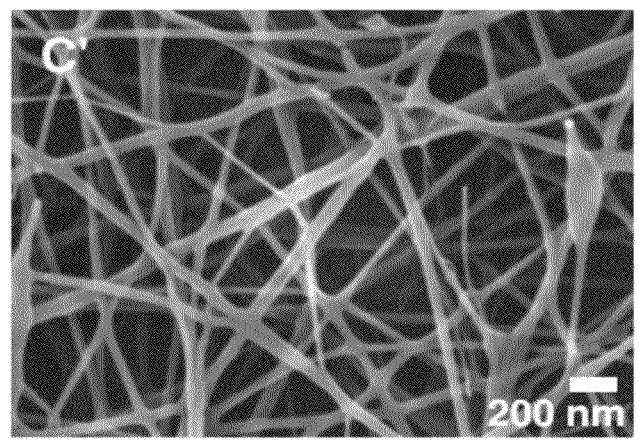

FIGS. 1A-1C' are scanning electron microscope (SEM) images of representative alginate-polyethylene oxide (PEO) fibers of the invention electrospun from alginate/PEO solutions containing 0.5 wt % Triton X-100 surfactant and 5 wt % DMSO co-solvent: FIG. 1A is an image of a representative alginate-PEO fiber spun from a solution having an alginate/PEO ratio of 70:30; FIG. 1A' is a higher magnification image of the image of FIG. 1A; FIG. 1B is an image of a representative alginate-PEO fiber spun from a solution having an alginate/PEO ratio of 80:20; FIG. 1B' is a higher magnification image of the image of FIG. 1B; FIG. 1C is an image of a representative alginate-PEO fiber spun from a solution having an alginate/PEO ratio of 90:10; and FIG. 3A' is a higher magnification image of the image of FIG. 3A;

Both dried and wet nanofibrous mats were evaluated for a stress-strain response using a microtensile testing machine designed for high-accuracy small-sample testing. Wet samples were prepared by incubating $CaCl_2$ crosslinked nanofibrous mats in DI water for 1 h at 37° C. immediately prior to the tensile test. The load cell had a loading range of ±30 g with an incremental accuracy of 0.001 g. The data were acquired through a computer interface connected to a load transducer (Model SS-2) and an electronic signal conditioner (PTC Electronics, Wyckoff, N.J.) on the test machine. The load was applied by a stepper motor system (Motion Group, Clovis, Calif.) controlled by a LabView routine written by the authors. Nanofibrous mats were cut in a rectangular shape with a cross-section of 60 $mm^2$. The tensile modulus was calculated from the stress-versus-strain curve.

FIG. 2A is a bar graph comparing the tensile moduli of representative alginate-PEO fibers of the invention electrospun from an 80:20 alginate/PEO solution: as spun fiber; calcium chloride crosslinked dried fiber; and calcium chloride crosslinked wet fiber.

Cell Culture.

The nanofibrous mats crosslinked with calcium chloride were mounted on cover glass (22 $mm^2$) and sterilized with ethylene oxide gas. The nanofibrous mats were fixed on glass coverslides using copper tapes (22 $mm^2$) and washed several times with 75% ethanol and DI water at neutral pH to remove residual solvents. $10^5$ chondrocyte (HTB-94) cells in 1 mL DMEM containing 10% fetal bovine serum, 50 IU $mL^{-1}$ penicillin, and 50 μg $mL^{-1}$ streptomycin were then seeded on each nanofibrous mat in 24-well culture plates. Cellular constructs were harvested after 3 days, washed extensively with PBS, and fixed with Karnovsky's fixative overnight at room temperature. All the samples were gradually dehydrated with 50, 75, 95, and 100% ethanol, for 2 h each. The samples were then dried using a critical-point dryer and coated with Au—Pd for SEM imaging.

FIGS. 2B and 2C are scanning electron microscope (SEM) images of representative alginate-polyethylene oxide (PEO) fibers of the invention electrospun from an 80:20 alginate/PEO solution after immersion in deionized (DI) water for 1 day and 15 days, respectively.

Cell Viability.

Cell viability was assessed using a Live/Dead Assay Kit (PA-3016, Molecular Probes). 100-150 μL of the Live/Dead assay reagent was added to cell-cultured alginate nanofibers on a glass coverslip (22 $mm^2$), and the coverslip was incubated for 45 min. The reagent contained the vital dye calcein-AM and nuclear stain ethidium homodimer-1 (both from the Live/Dead Assay Kit). Calcein-AM is a non-fluorescent, cell-permeant fluorescein derivative, which is converted by cellular enzymes into cell-impermeant and highly fluorescent calcein. Calcein accumulates inside live cells with intact membranes and renders the cells fluorescent green. Ethidium-homodimer-1 enters dead cells with damaged membranes and undergoes a 40-fold enhancement of fluorescence upon binding to their DNA, causing the nuclei of dead cells to fluoresce red. This double-staining showed both live and dead cells attached on the scaffold. The wet coverslip was inverted and placed on the microscope slide. Images of chondrocyte cells on nanofibers were acquired using an inverted fluorescent microscope equipped with a charge-coupled device (CCD) camera. Cellular viability was quantified following the manufacturer's instruction.

FIGS. 3A-3C compare the in vitro cellular compatibility of alginate fibers electrospun from an 80:20 alginate/PEO solution: FIG. 3A is a scanning electron microscope image of chondrocytes grown on alginate-PEO fibers; FIG. 3B is a higher magnification image of the image of FIG. 3B; and FIG. 3C is a fluorescence image of cells on fibers with the Live/Dead cell stain.

Example 2

The Preparation and Characterization of Representative Crosslinked Alginate Fibers In this example, the preparation and characterization of representative alginate fibers of the invention, crosslinked alginate-PEO fibers, is described.

Materials.

Alginic acid sodium salt from brown algae having medium viscosity was purchased from Sigma-Aldrich chemical Co. Based on the supplier's information, the alginate with viscosity about 350 cP (2% solution, 25° C.) is polyuronic acid composed primarily of linear and hydrophilic anhydro-β-D-mannuronic acid residues with 1→4 linkage. Polyethylene oxide (PEO) (Mw=900 kDa), epichlorohydrin, glutaraldehyde, hexamethylene diisocyanate (HMDI), 2-(N-morpholino)ethanesulfonic acid hydrate (MES) buffer, 1-hydroxybenzotriazole (HOBt), 1-ethyl-3-[3-(dimethylamino)propyl]carbodiimide (EDC), and adipic acid hydrazide (AAD) were also obtained from Sigma-Aldrich Chemical Co. Triton X-100 was purchased from VWR Co. Two different buffers, phosphate buffered saline (PBS) and simulated body fluid (SBF), were prepared in the lab using buffer constituents purchased from Sigma and J.T. Baker Chemical Co. SBF with an ion concentration proximately equal to that of human blood plasma was prepared by dissolving reagent grade NaCl, NaHCO$_3$, KCl, K$_2$HPO$_4$.3H$_2$O, MgCl$_2$.6H$_2$O, CaCl$_2$, and Na$_2$SO$_4$ in distilled water. They were buffered at pH 7.4 with tris(hydroxymethyl)aminomethane ((CH$_2$OH)$_3$CNH$_2$) and hydrochloric acid.

Preparation of the Electrospinning Solution.

4 wt % alginate solutions and 4 wt % PEO solutions were first prepared separately by dissolving alginate and PEO in deionized water, followed by centrifugation to remove air bubbles. Alginate and PEO solutions of different proportions were then mixed to obtain the blend solutions with weight ratios of alginate to PEO ranging from 40:60 to 90:10, and the resultant solutions were stirred for 3 h. Solutions containing 0-1.0 wt % of Triton X-100 and 0-10 wt % of dimethylsulfoxide (DMSO) were mixed with alginate/PEO solutions, and the mixtures were stirred for additional 3 h and centrifuged to remove air bubbles before use.

Electrospinning of Fibers.

The electrospinning process used in this study was as described above in Example 1. Briefly, the solution was fed into a 3 ml disposable syringe fitted with a pipette tip of 0.5 mm in diameter. A DC voltage of 10-15 kV (High DC power supply, Del Electronics Corp.) was applied between the syringe tip and a cylindrical collector covered with aluminum foil. The cylinder had a diameter of 7 cm and was driven by a DC motor with controllable speed. The typical distance between the syringe tip and the grounded collector was 17-20 cm. During the spinning process, the pendant droplet at the syringe tip was split by a repulsion force set by the charge in the droplet, and formed a jet of a cone-like shape traveling towards the collector, during which time the solvent evaporated and polymer fibers deposited on the collector in form of a nonwoven fibrous mat. All the spinning experiments and drying of as-spun nanofibers were conducted at room temperature. The diameter, morphology, and surface topography of the nanofibers were examined using SEM (JEOL JSM-840A) at an accelerating voltage of 10 kV. Electrospun nanofibers were sputter-coated with Au/Pd prior to SEM analysis. The mean diameter of electrospun nanofibers was determined by measuring the diameters of nanofibers at 100 different points in a 645×484 SEM image. A Philips CM 100 transmission electron microscope (TEM) was used to observe internal features of nanofibers. For TEM observation, a thin fibrous membrane was sandwiched in PELCO folding grids and images were acquired at the edges of the membrane. As the intrinsic difference in electron density between alginate and PEO polymers provided adequate contrast, no staining was needed.

FIGS. 6A-6D are images of electrospun alginate/PEO fibers from 80:20 alginate/PEO solutions: FIG. 6A is a SEM image of fibers obtained by adding Triton X-100 (0.5 wt %); FIG. 6B is a SEM image of fibers obtained by adding Triton X-100 (0.5 wt %) and DMSO (5.0 wt %); FIG. 6C is a transmission electron microscope (TEM) image of the fibers of FIG. 6B; and FIG. 6D is a higher magnification TEM image of the fibers of FIG. 6B.

Characterization of Stability of Alginate Solution.

The shear viscosities of the solutions of different alginate/PEO ratios were measured in a shear rate range of 5-500 s$^{-1}$ using a Haake Viscometer (VT550) equipped with double concentric cylinder-type SP2P sensors. FTIR spectroscopy and UV-VIS spectroscopy were utilized to identify the decrease in molecular weight and change in molecular structure of alginate in aqueous solution over storage time, which directly affects the spinnability of the solution. For measurements of changes in solution viscosity over a time course, the solution was prepared as described above and maintained at room temperature. A 10 ml sample was periodically taken out from the solution and the samples collected at different times were stored in a freezer at −20° C. Viscosity of each sample was measured immediately after defrosting the sample. For UV and FTIR experiments, powdered alginate samples were first prepared by precipitating the alginate solutions collected at different times with ethanol. The samples were washed with a mixture of ethanol/water (80/20 v/v) and subsequently dried under vacuum. For UV measurements, 0.5 wt % alginate solutions in DI water were prepared and their UV absorption spectra were acquired using a UV-Vis Spectrophotometer (Hewlett Packard 8452A Diode Array) operating at 200-400 nm with 2 nm resolutions. For FTIR analysis, samples were prepared by mixing alginate powder with KBr at alginate/KBr w/w ratio of 1/60 using a macro KBr die kit. The solid pellet was placed in a magnetic holder, and the system was purged with nitrogen before testing. Polarized FTIR spectra of 200 scans at 4 cm$^{-1}$ resolutions were obtained using a Nicolet 5DX spectrometer equipped with a DTGS detector and a solid transmission sample compartment. Spectrum analysis and display were performed using standard Nicolet and Microcal Origin software.

FIG. 7A is a graph illustrating zero shear viscosity of a 4 wt % alginate solution as a function of storage time. FIG. 7B compares the infrared (FTIR) spectra of the 4 wt % alginate solution as a function of storage time (Day 6, 10, 15, 20, and 30) to the infrared spectrum of as-received alginate powder (Control). FIG. 7C compares the ultraviolet (UV) absorbance spectra of the 4 wt % alginate solution as a function of storage time (Day 6, 10, 15, 20, and 30) to the absorbance spectrum of as-received alginate powder (Control).

Crosslinked Fibrous Mats.

Electrospun nanofibrous mats were first crosslinked using CaCl$_2$ solution at room temperature and then optionally crosslinked using one of four methods described below. Nanofibrous mats were immersed in ethanol for 5 min and then in saturated solution of CaCl$_2$ in 75% ethanol for 10 min. The samples were then incubated in an aqueous CaCl$_2$ solution for 1 h and immersed in DI water for additional 1 h, followed by rinsing with excess DI water to remove unreacted CaCl$_2$. After washing with absolute ethanol, the samples were dried at room temperature.

Epichlorohydrin Crosslinking.

Dried nanofibrous mats were soaked in a suspension containing 5M epichlorohydrin and 0.1M NaOH in 50% ethanol. The crosslinking reaction was allowed to proceed for 24 h and stopped by addition of 5M HCl. Crosslinked nanofibrous mats were washed with 75% ethanol and then with excess DI water. The samples were dried under reduced pressure at room temperature.

Glutaraldehyde Crosslinking.

Nanofibrous mats were immersed in 50 wt % ethanol containing 250 mM of glutaraldehyde and 0.05M HCl. The crosslinking reaction was allowed to proceed at room temperature for 48 h. Upon the reaction completion, nanofibrous mats were washed with excess DI water and dried under reduced pressure at room temperature.

Hexamethylene Diisocyanate (HMDI) Crosslinking.

Dried nanofibrous mats were soaked in and rinsed with a DMSO/DMF (1:1 v/v) mixture. A mixture of 5 wt % solution of hexamethylene diisocyanate (HMDI) and 0.5 g of triethylamine (TAE) was prepared in DMSO/DMF (1:1 v/v) and poured on the top of the fiber mat. The crosslinking reaction was allowed to proceed at room temperature for 48 h. Excess reactants and byproducts were washed away from samples by extracting with tetrahydrofuran (THF) for 5 h using a Sohxlet apparatus, and the samples were dried at 40° C. under vacuum for 24 h.

Adipic Acid Hydrazide (ADA) Crosslinking.

Nanofibrous mats were soaked in 2-morpholinoethanesulfonic acid (MES) buffer (at pH 6.5) containing 5 mM 1-hydroxybenzotriazole for 2 h, and 5 mM EDC was then added into the mixture. After the samples were soaked in the mixture for additional 1 h, 1M AAD was added. The crosslinking reaction was allowed to proceed for 20 h at room temperature on a rocking shaker, and upon completion of the reaction the samples were washed with excess DI water. The nanofibrous mats were then dried under reduced pressure.

To test the stability of nanofibrous mats in aqueous ionic environments over time, crosslinked nanofibrous mats were incubated in SBF (pH=7.5) at room temperature. Samples were collected periodically from the incubated solution and dried at room temperature after three washes with DI water/ethanol mixture. Similar experiment was also performed by incubating the crosslinked nanofibrous mat in PBS (pH=7.5). The integrity of alginate nanofibers were examined by morphological changes observed under SEM.

FIGS. 8A and 8B are SEM images of a representative ionically (calcium chloride) crosslinked alginate (alginate/PEO 80:20) fibrous mat of the invention incubated in DI water (FIG. 8A) and SBF (FIG. 8B) for seven days at 37° C.

FIGS. 8C-8F are SEM images of representative crosslinked alginate (alginate/PEO 80:20) fibrous mats of the invention incubated in SBF (pH 7.4) for seven days at 37° C.: the fibrous mats were first ionically crosslinked with calcium chloride followed by covalent crosslinking with epichlorohydrin (FIG. 8C), glutaraldehyde (FIG. 8D), hexamethylene diisocyanate (HMDI) (FIG. 8E), or adipic acid hydrazide (ADA) (FIG. 8F).

While illustrative embodiments have been illustrated and described, it will be appreciated that various changes can be made therein without departing from the spirit and scope of the invention.

The embodiments of the invention in which an exclusive property or privilege is claimed are defined as follows:

1. A crosslinked fiber, comprising alginate and a hydrophilic polymer, wherein the fiber comprises from about 30 to about 95 weight percent alginate based on the total weight of the fiber.

2. The fiber of claim 1 having a diameter of from about 20 to about 2000 nm.

3. The fiber of claim 1, wherein the hydrophilic polymer is selected from the group consisting of a poly(alkylene oxide), a polyvinyl alcohol, and a polycarboxylic acid polymer.

4. The fiber of claim 3, wherein the poly(alkylene oxide) is polyethylene oxide.

5. The fiber of claim 3, wherein the poly(alkylene oxide) has a molecular weight of from about 50 kDa to about 1000 kDa.

6. The fiber of claim 3, comprising from about 5 to about 30 weight percent poly(alkylene oxide) based on the total weight of the fiber.

7. The fiber of claim 1, wherein the fiber is crosslinked with an ionic crosslinking agent.

8. The fiber of claim 7, wherein the ionic crosslinking agent is a metal ion selected from the group consisting of calcium (2), barium (2), strontium (2), copper (2), zinc (2), magnesium (2), manganese (2), cobalt (2), lead (2), iron (3), and aluminum (3) ions.

9. The fiber of claim 7 further crosslinked with a covalent crosslinking agent.

10. The fiber of claim 9, wherein the covalent crosslinking agent is a bifunctional crosslinking agent selected from the group consisting of carbodiimides, allyl halide oxides, dialdehydes, diamines, and diisocyanates.

11. The fiber of claim 9, wherein the covalent crosslinking agent is selected from the group consisting of epichlorohydrin, gluteraldehyde, hexamethylene diisocyanate, adipic acid hydrazide, and 1-ethyl-3-(3-dimethylaminopropyl)carbodiimide hydrochloride.

12. The fiber of claim 1, wherein the fiber is crosslinked with a covalent crosslinking agent.

13. A fibrous scaffold, comprising a plurality of the fibers of claim 1.

14. The scaffold of claim 13 further comprising chitosan.

15. The scaffold of claim 13 further comprising collagen.

16. The scaffold of claim 13 further comprising a biologically active amino acid molecule selected from the group consisting of growth factors, fibronectin, laminin, vitronectin, integrins, nucleic acid molecules, lipids, sugars, antisense molecules, anti-inflammatory agents, immunomodulatory agents, molecules that promote cell migration, molecules that promote cell division, molecules that promote cell proliferation and differentiation, molecules that stimulate phenotypic modification of cells, molecules that promote angiogenesis, molecules that promote vascularization, and molecules that promote extracellular matrix disposition.

17. The scaffold of claim 13 further comprising a signaling ligand selected from the group consisting of members of the TGF-β family, bone morphogenic proteins, fibroblast growth factors-1 and -2, platelet-derived growth factor-AA and -BB, and platelet rich plasma and vascular endothelial cell-derived growth factor.

18. An implantable device, comprising the fiber of claim 1.

19. The device of claim 18, wherein the device is a cell transplantation device, a drug delivery device, a wound dressing, a hemostat, a surgically implantable device for repairing a damaged cartilage in mammalian articulating joints, a fabric barrier to hyperplasia and tissue adhesion, a vascular prosthesis, a nerve graft, a spinal fusion cage, or a skin substitute.

* * * * *